US012588860B2

(12) United States Patent　　　　(10) Patent No.:　US 12,588,860 B2
Nay et al.　　　　　　　　　　　　(45) Date of Patent:　Mar. 31, 2026

(54) SYSTEM AND METHOD FOR INTRAOPERATIVE GUIDANCE

(71) Applicant: NEURALYTIX, LLC, Brighton, MI (US)

(72) Inventors: David S. Nay, Novi, MI (US); Christopher Wybo, Brighton, MI (US)

(73) Assignee: Neuralytix, LLC, Fruita, CO (US)

( * ) Notice: Subject to any disclaimer, the term of this patent is extended or adjusted under 35 U.S.C. 154(b) by 0 days.

(21) Appl. No.: 19/098,512

(22) Filed: Apr. 2, 2025

(65) Prior Publication Data

US 2026/0041364 A1　　Feb. 12, 2026

Related U.S. Application Data

(63) Continuation of application No. 18/799,984, filed on Aug. 9, 2024, now Pat. No. 12,279,880.

(51) Int. Cl.
　　*A61B 5/00*　　　　(2006.01)
　　*G16H 10/60*　　　(2018.01)
　　　　　　(Continued)

(52) U.S. Cl.
　　CPC .......... *A61B 5/4052* (2013.01); *A61B 5/4848* (2013.01); *A61B 5/6804* (2013.01);
　　　　　　(Continued)

(58) Field of Classification Search
　　CPC .... A61B 5/4052; A61B 5/4848; A61B 5/1107
　　See application file for complete search history.

(56) References Cited

U.S. PATENT DOCUMENTS

2008/0183190 A1*　7/2008　Adcox ................... G16H 30/40
　　　　　　　　　　　　　　　　　　　　606/130
2010/0317942 A1　12/2010　Cinbis et al.
　　　　　　　　(Continued)

FOREIGN PATENT DOCUMENTS

KR　　20240009921 A　　1/2024
WO　　　2016118752 A1　　7/2016
WO　　　2023283568 A1　　1/2023

OTHER PUBLICATIONS

The International Search Report and Written Opinion for an International Application No. PCT/US2025/041537, dated Dec. 9, 2025.
(Continued)

*Primary Examiner* — Tammie K Marlen
(74) *Attorney, Agent, or Firm* — Quinn IP Law

(57)　　　　　ABSTRACT

A method for intraoperative guidance during a surgical procedure involving a nerve includes receiving real-time image data from an intraoperative imaging modality, the real-time image data depicting anatomical structures within an intracorporeal treatment area including the nerve; determining at least one nerve function parameter indicative of nerve health; and controlling a display device to concurrently present a visual output comprising both a visual representation derived from the real-time image data and a visual indication of the determined at least one nerve function parameter. The concurrently presented visual output facilitates assessment of the nerve relative to the anatomical structures during the surgical procedure.

19 Claims, 7 Drawing Sheets

(51) Int. Cl.
   *G16H 50/30* (2018.01)
   *G16H 50/70* (2018.01)
(52) U.S. Cl.
   CPC .......... *A61B 5/7264* (2013.01); *A61B 5/7275*
      (2013.01); *A61B 5/7405* (2013.01); *A61B*
         *5/743* (2013.01); *A61B 5/746* (2013.01);
            *G16H 10/60* (2018.01); *G16H 50/30*
         (2018.01); *G16H 50/70* (2018.01); *A61B*
            *2560/0462* (2013.01); *A61B 2562/0219*
                                          (2013.01)

(56) References Cited

U.S. PATENT DOCUMENTS

| | | | |
|---|---|---|---|
| 2013/0123659 A1* | 5/2013 | Bartol .................. | A61B 5/1104 |
| | | | 600/554 |
| 2014/0073986 A1 | 3/2014 | Bartol et al. | |
| 2017/0020450 A1* | 1/2017 | Wybo .................. | A61B 5/4893 |
| 2017/0056642 A1 | 3/2017 | Moffitt et al. | |
| 2019/0000349 A1 | 1/2019 | Narayan et al. | |
| 2019/0290149 A1 | 9/2019 | Farquhar | |
| 2022/0110579 A1 | 4/2022 | Langer et al. | |
| 2022/0142555 A1 | 5/2022 | Taylor | |

OTHER PUBLICATIONS

The International Search Report and Written Opinion for an International Application No. PCT/US2025/041538, dated Dec. 10, 2025.

* cited by examiner

SYSTEM AND METHOD FOR INTRAOPERATIVE GUIDANCE

CROSS REFERENCE TO RELATED APPLICATIONS

The present application is a continuation of U.S. patent application Ser. No. 18/799,984, filed 9 Aug. 2024, which is incorporated by reference in its entirety.

TECHNICAL FIELD

The present disclosure relates generally to systems and techniques for intraoperatively determining the health of a nerve during a surgical procedure.

BACKGROUND

Spinal decompression surgery is a critical intervention for patients suffering from nerve compression caused by conditions such as spinal stenosis (attributable to conditions such as herniated discs, osteophytes, or degenerative disc disease). The primary goal of spinal decompression is to alleviate pressure on the affected nerve roots, thereby reducing pain, restoring neurological function, and improving the patient's quality of life.

Spinal decompression procedures can be categorized into three main types: direct decompression, indirect decompression, and decompression with fusion. Direct or 'non-instrumented' decompression involves the surgeon directly removing tissue that is impinging the nerve, often by increasing the size of the spinal foramen. Indirect decompression uses devices like interspinous spacers (e.g., between adjacent posterior spinous processes) to indirectly enlarge the foramen and decompress the nerve. In cases of significant instability or when direct or indirect decompression alone is insufficient, a fusion procedure may be performed to stabilize the spine and decompress the nerve by fusing adjacent vertebrae together.

Presently, the success of certain spinal decompression procedures relies heavily on the surgeon's ability to accurately determine the degree of compression and the optimal extent of decompression required for each individual patient. For this, surgeons typically rely on their clinical judgment, experience, and visual inspection of the surgical site to guide the decompression process. This reliance on experience, and resulting procedural variability, presents legitimate risks of under-decompression, where the nerve remains partially compressed, or over-decompression, which can lead to spinal instability, dural tears, or other such complications. In either instance, the patient may not experience complete relief and may require subsequent procedures such as pain injections, revision surgeries, or even a complete fusion.

The lack of objective, real-time guidance during spinal decompression surgery presents a major challenge in optimizing patient outcomes. As such, there is a need for a reliable, evidence-based tool that can provide continuous feedback on nerve function while guiding a procedure and surgeon toward the optimal decompression endpoint.

SUMMARY

The present disclosure describes a system and method for assessing nerve health during spinal surgical procedures, particularly spinal decompression surgeries. The system includes a stimulator configured to deliver electrical stimuli to a nerve, a sensor configured to detect muscle responses evoked by the electrical stimuli, a display device, and a processor in communication with the stimulator, sensor, and display device.

The processor is configured to control the stimulator to deliver electrical stimuli to the nerve, determine nerve function parameters based on the muscle responses detected by the sensor, compare the determined parameters to predefined target ranges, and control the display to provide real-time feedback. The nerve function parameters may include a minimum electrical current required to evoke a detectable muscle response (stimulation threshold), a minimum electrical current required to evoke a supramaximal muscle response (supramaximal stimulation threshold), and the magnitude of the supramaximal muscle response.

To efficiently determine these parameters, the system employs sophisticated algorithms. A binary search algorithm may be used to efficiently locate the minimum stimulation threshold, starting with an initial current range and iteratively narrowing it based on detected responses. An adaptive search algorithm, leveraging data from the binary search, may then be used to determine the supramaximal stimulation threshold. This approach minimizes the number of stimuli required, reducing patient discomfort and the risk of nerve fatigue.

The predefined target ranges may be indicative of a fully decompressed nerve and typically include a range of electrical currents that encompasses 2 mA to 3 mA for the stimulation threshold. In some embodiments, however, the system also provides for subject-specific target ranges determined based on individual attributes such as age, body mass index (BMI), and pre-operative neurological function assessment.

In some embodiments, the system may be integrated with a comprehensive database of historical patient data. This database may contain nerve function measurements from previous surgical procedures, subject-specific attributes, and associated surgical outcomes. The processor can access this database to identify a subset of subjects with attributes similar to the current patient. It may then define individualized target ranges based on nerve function parameters associated with successful outcomes in this subset, allowing for highly personalized patient care.

The system may further employ advanced machine learning techniques to analyze the historical patient data, identify complex patterns between pre-operative characteristics, intraoperative nerve function measurements, and post-operative outcomes. Such algorithms may continuously refine the predictive models used to generate individualized target ranges and risk profiles, improving their accuracy over time as new data is incorporated.

The system may generate statistical risk profiles that correlate nerve function measurements with probabilities of surgical complications. These may include specific risks such as destabilization of the spine, dural tears, blood clots, cerebrospinal fluid leaks, and infections. The processor may be configured to determine a statistical risk of complications based on the nerve function parameters and subject-specific attributes, and control the display to provide a clear indication of these risks.

The display may provide a sophisticated graphical user interface for presenting this information to the surgeon. It may include color-coded indicators, graphical representations of nerve function parameters relative to target ranges, and visual representations of risk profiles. The interface may also allow for customization, enabling surgeons to focus on specific complication risks they deem most relevant to a particular procedure.

In some embodiments, the sensor comprises a mechanical sensor with an accelerometer configured to detect a mechanical muscle response evoked by the electrical stimuli. This mechanomyography (MMG) approach allows for precise detection of muscle responses without the need for needle electrodes and while providing a significantly improved signal-to-noise ratio when compared to electromyography (EMG).

The disclosure also describes the calculation of a composite nerve function index. This index may comprise a weighted average of multiple nerve function parameters, providing a comprehensive measure of nerve health. The weighting of different parameters may be adjusted based on their relative importance in assessing nerve function, as determined through empirical studies or expert consensus.

The system may be integrated with intraoperative imaging modalities such as fluoroscopy or ultrasound. This integration allows surgeons to visualize anatomical structures in real-time while simultaneously monitoring nerve function, providing a more comprehensive view of the surgical field.

Furthermore, the disclosure includes mechanisms for post-operative data collection and system improvement. After each procedure, the system can receive and incorporate post-operative outcome data, updating the database and refining its predictive models. This continuous learning process allows the system to adapt and improve over time, potentially leading to better surgical outcomes and reduced complications in future procedures.

The method of operating the system includes delivering electrical stimuli to a nerve, detecting muscle responses evoked by the electrical stimuli, determining nerve function parameters based on the detected muscle responses, comparing the determined parameters to predefined or individualized target ranges, and controlling a display to provide real-time feedback to the surgeon.

While primarily described in the context of spinal decompression surgery, the principles and methods of this system can be adapted for use in other surgical and non-surgical procedures involving nerve monitoring, such as peripheral nerve decompression surgeries or tumor resections near critical nerve structures.

By providing surgeons with objective, real-time, and personalized feedback on nerve function during spinal decompression procedures, this technology aims to optimize the extent of decompression, improve surgical outcomes, reduce complications, and ultimately enhance patient care in the field of spinal surgery.

DETAILED DESCRIPTION

The presently described technology presents a diagnostic system that enables surgeons functionally monitor the health and/or responsiveness of a compressed nerve during a surgical decompression procedure. Through such monitoring, the present system provides spinal surgeons with unique procedural insights that can be used to reduce the risk of under- or over-decompression and thus improve overall surgical success rates. Further, in some embodiments, the system can allow the surgeon to tailor a spinal decompression procedure to each patient's unique anatomy and neurological condition.

Optimizing the degree of surgical decompression though intraoperative monitoring may lead to decreased complication rates, shorter hospital stays, lower healthcare costs associated with revision surgeries, prolonged recovery, and even subsequently required vertebral fusion procedures. Additionally, the insights gained from the data collected by the present diagnostic system could contribute to the advancement of new spinal decompression techniques and the understanding of nerve function in various pathological conditions.

System 10

Figure 1:
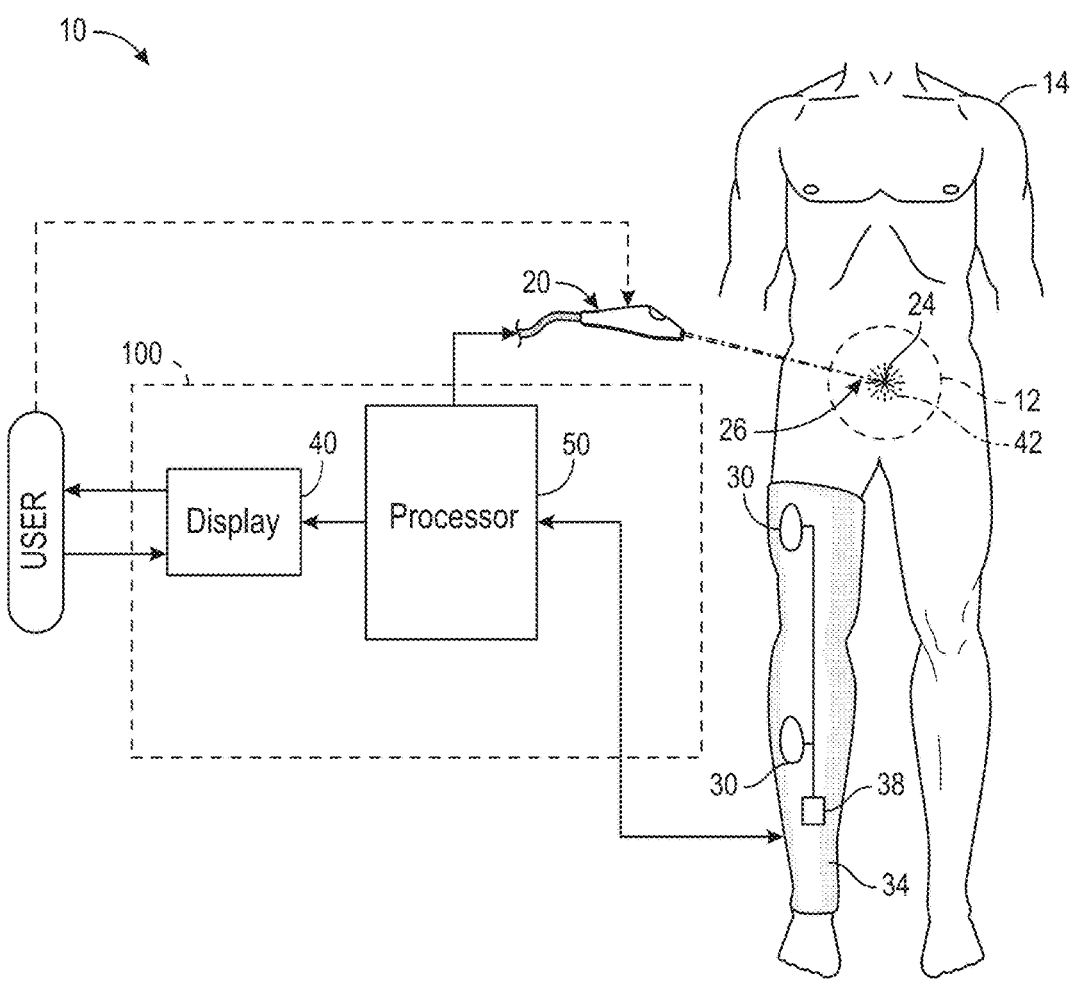
FIG. 1 schematically illustrates an embodiment of a neural monitoring system.

Referring to the drawings, wherein like reference numerals are used to identify like or identical components in the various views, FIG. 1 schematically illustrates a neural monitoring system 10 that is designed to optimize spinal decompression surgery by providing a real-time functional assessment of a nerve to a user/surgeon/healthcare provider (generally referred to as a "user"). As may be appreciated, the nerve exists within an intracorporeal treatment area 12 of a subject 14 and innervates a distal muscle group of the subject 14).

In its most general sense, the system 10 comprises four main components: a stimulator 20, a neuromuscular sensor (NMS) 30, an output device (e.g., a display 40), and a host processor 50. The stimulator 20 delivers an electrical stimulus 22 to a compressed nerve within the intracorporeal treatment area 12. The NMS 30 detects muscle responses evoked by this electrical stimulus (i.e., an "artificially induced neuromuscular response"). The display 40 provides real-time feedback to the user/surgeon. The host processor 50 (also just referred to as the "processor 50") coordinates these components, being in electrical communication with the stimulator 20, sensor 30, and display 40. In some embodiments, the display 40 and processor 50 may be integrated into a single control unit 100, which can be adapted for mounting adjacent to the subject.

As used herein, an "artificially induced neuromuscular response" is a response of a muscle to an artificial/non-biological stimulus applied to a nerve innervating that muscle. In general, the response is "artificially induced" because the nerve is depolarized directly by the stimulus, instead of, for example, the stimulus being received through an intermediate sensory means (e.g., sight, sound, taste, smell, and touch). An example of a stimulus that may cause an "artificially-induced" muscle response may include an electrical current applied directly to the nerve or to intracorporeal tissue or fluid immediately surrounding the nerve. In such an example, if the applied electrical current is sufficiently strong and/or sufficiently close to the nerve, it may cause the nerve to involuntarily depolarize (resulting in a corresponding contraction of the muscle or muscles innervated by that nerve). Other examples of such "artificial stimuli" may involve mechanically-induced depolarization (e.g., physically stretching or compressing a nerve, such as with a tissue retractor), thermally-induced depolarization (e.g., through ultrasonic cautery), or chemically-induced depolarization (e.g., through the application of a chemical agent to the tissue surrounding the nerve).

During an artificially induced neuromuscular response, a muscle innervated by the artificially depolarized nerve may physically contract or relax (i.e., a mechanical response) and/or the electrical potential throughout the muscle may also be altered. Mechanical responses may primarily occur along a longitudinal direction of the muscle (i.e., a direction aligned with the constituent fibers of the muscle), though may further result in a respective swelling/relaxing of the muscle in a lateral direction (which may be substantially normal to the skin for most skeletal muscles). This local movement of the muscle during an artificially-induced mechanical muscle response may be measured relative to the position of the muscle when in a non-stimulated state.

Simulator 20

As noted above, the system 10 may include one or more elongate nerve stimulators that are capable of selectively providing a stimulus 22 within the intracorporeal treatment area 12 of the subject 14. In one configuration, the stimulator 20 may resemble a traditional surgical instrument such as a k-wire, a ball-tip probe, a needle, or a catheter that is intended to extend into the intracorporeal space of the subject 14. To accomplish this, the stimulator 20 includes an elongate body with an electrode 24 disposed on its distal end portion 26. The electrode 24 may be in electrical communication with the processor 50 and may be selectively electrified by the processor 50 to provide an electrical stimulus 22 to intracorporeal tissue of the subject. In other configurations, the stimulator 20 may comprise a dilator, retractor, clip, cautery probe, pedicle screw, robotic end effector, or any other medical instrument that may be used in an invasive medical procedure.

The electrode 24 may be an electrically conductive pad or surface of the stimulator 20 that is intended to contact tissue within the intracorporeal treatment area 12 during the procedure. In some embodiments, the electrode 24 may be a distinct element, such as a gold contact that is overlaid or printed onto the body or tip of the stimulator 20. In other embodiments, the electrode 24 may simply be an uninsulated/exposed portion of the stimulator 20 that is electrically conductive and able to outwardly transmit an electrical current to surrounding tissue/fluids.

In some embodiments, the stimulator 20 may be particularly designed to access and electrically stimulate a nerve that is compressed within a spinal foramen. Such a design may include a stimulator with specialized geometry that allows the distal tip of the stimulator to extend around a portion of the spinal lamina from either an upper (superior)

or lower (inferior) direction, thus enabling direct access to the nerve within the foramen.

Neuromuscular Sensor 30

The neuromuscular sensor 30 (NMS 30) (generically referred to as the sensor 30) is the portion of the system 10 that directly contacts the subject 14 and is responsible for, at a minimum, sensing and measuring responses of the subject's muscles to the applied electrical stimulus 22 and providing a corresponding MMG output signal 32 to the processor 50.

A carrier material 34 is provided to operatively hold each provided sensor 30 in direct mechanical communication with the external skin surface of the subject 14. The carrier material 34 may be, for example, an adhesive pad, a pocketed patch, a cuff, and/or a sleeve that is operative to receive the sensor 30 while not substantially restricting the motion of the muscle.

In some embodiments the carrier material 34 may encapsulate and/or form a sterile barrier around the NMS 30. This may promote cost-effective reusability of the NMS 30 without subjecting it to the same sterilization requirements as if it were directly within the sterile field (i.e., absent a suitable barrier material). In some embodiments, the carrier material 34 may be a separate therapeutic or diagnostic device that is already common in surgical applications. For example, in a spinal procedure involving one or more of the L2-S1 vertebrae, it is known that nerve roots innervating the leg muscles may lie within the surgical area. During such procedures, however, compression-type anti-embolism stockings (Thrombo-Embolic-Deterrent ("TED") hose) are typically provided around a subject's legs and feet to discourage blood clot formation. Thus, in one embodiment the carrier material 34 may be an elastic sleeve/stocking configured to apply a compressive force to the subject's leg when worn, thus eliminating the need for separate TED hose. Such a compression against the subject may present itself as an elastic tension/strain in the carrier material itself (also referred to as a "tension fit"). In surgical procedures performed higher on the spine, the carrier material 34 may include, for example, a blood pressure cuff worn around the subject's arm (or else may include functionality similar to that of a standard blood pressure cuff). In these examples, the carrier material 34 serves a function outside of that of a dedicated neuromuscular sensing device, and thus provides efficiencies in pre-op preparation and planning, while also allowing monitoring access on sometimes crowded limbs.

Figure 2:
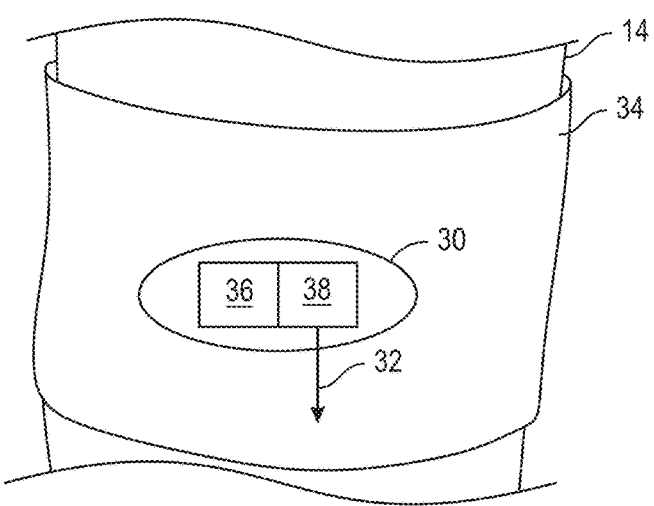
FIG. 2 schematically illustrates an embodiment of a neuromuscular sensor.

In various embodiments, such as shown in FIG. 2, each NMS 30 may comprise a mechanical sensor 36 that is operative to monitor the relative movement of the muscle that the NMS 30 is most closely coupled with. Examples of suitable mechanical sensors 36 include, strain gauges, a pressure/force transducers, position encoders, accelerometers, piezoelectric materials, or any other transducer or combination of transducers that may convert a physical motion into a variable analog or digital electrical signal. In one particular embodiment, the mechanical sensor 36 may be an accelerometer configured to detect a mechanical muscle response evoked by the electrical stimuli. In some embodiments, an NMS 30 may alternatively or additionally include one or more transdermal electrodes, needle electrodes, or other such sensors that may be operative to monitor mechanical or electrical response parameters of the subject.

In some embodiments, each sensor 30 (or collection of sensors 30) may include a local or onboard processor 38 (i.e., local to the sensor 30) that is in communication with the mechanical sensor 36 of that NMS 30. The local processor 38 may be configured to, for example, pre-process and/or filter data acquired from the mechanical sensor 36 and transmit an MMG output signal 32 to the host processor 50. The MMG output signal 32 may be a digital or analog signal that is representative of the output (or filtered output) of the mechanical sensor 36. The local processor 38 may further include suitable communication circuitry to facilitate unidirectional or bidirectional digital communication with the host processor 50.

In general, processors used with the present system 10 (e.g., processors 38, 50) may be embodied as one or multiple digital computers, data processing devices, and/or digital signal processors (DSPs), which may have one or more microcontrollers or central processing units (CPUs), read only memory (ROM), random access memory (RAM), electrically-erasable programmable read only memory (EE-PROM), flash memory, high-speed clocks, analog-to-digital (A/D) circuitry, digital-to-analog (D/A) circuitry, input/output (I/O) circuitry, and/or signal conditioning and buffering electronics.

Control Unit 100

As noted above, the system 10 may include both a display 40 and a processor 50 that, in some embodiments, may be combined into a common housing or control unit 100. In other embodiments, the control unit 100 may include the host processor 50 without an integrated display 40, though it may then include circuitry operative to communicate with an external display, third party device having a display, or a software application.

In a general sense, the host processor 50 is a special purpose device that is configured to transmit an electrical stimulus 22 to the stimulator 20, monitor the sensor 30 for the occurrence of an artificially induced neuromuscular response to the stimulus 22, determine one or more bioelectric or functional parameters of the nerve via the administered stimulus 22 and sensed response, and provide feedback about the nerve to the user/surgeon via the display 40.

In embodiments having an integrated display, the display 40 may include an LCD or LED-type display that is configured to provide the user/surgeon with a visual user interface. The display 40 may be capable of generating one or more visual alerts to notify the surgeon when specific nerve function thresholds are reached. These alerts may include color-coded indicators, flashing elements, pop-up notifications on the display, or graphical representation of a threshold being crossed. In some embodiments, the system may be configured to generate an audible or visual alert if the measured nerve function parameter, such as the minimum stimulation current, falls within the target range. Additionally, in some embodiments, the control unit 100 may be equipped with speakers or other sound-generating devices to provide audible alerts. These audible alerts can be in the form of distinct tones, verbal announcements, or varying patterns or frequencies of sounds to indicate different stages of nerve decompression or when target ranges are achieved.

Figure 3:
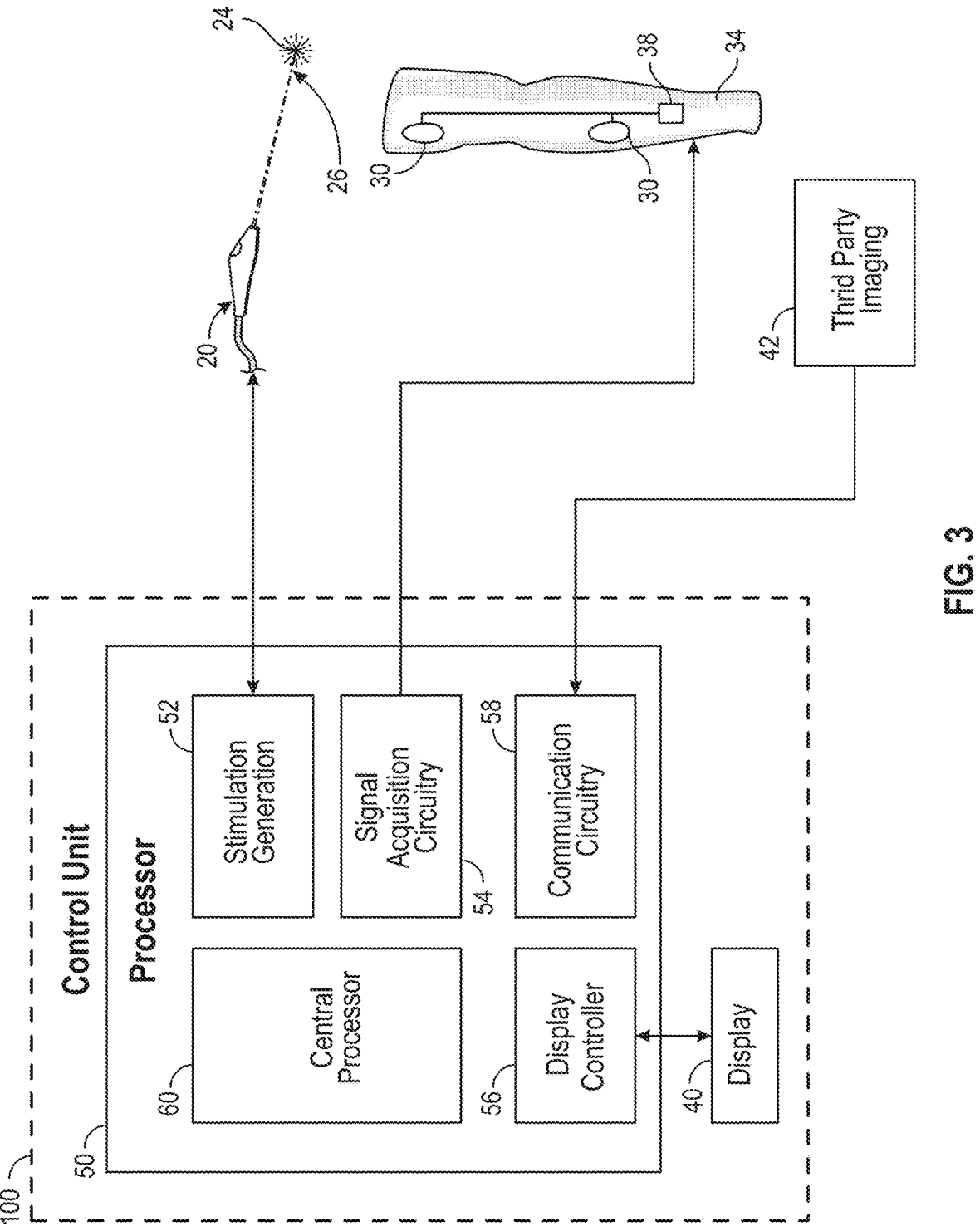
FIG. 3 schematically illustrates a functional diagram of an embodiment of a control unit.

Referring to FIG. 3, in some embodiments, host processor 50 may include one or more functional units or modules that provide specialized functionality or capabilities to the processor 50. Each functional unit or module may comprise the requisite hardware, circuitry, software, firmware, or combinations thereof to perform the intended function. Such modules may include, for example, a stimulation generator 52, signal acquisition circuitry 54, a display controller 56, and communications circuitry 58. Each of these functional units may operate at the direction and coordination of a supervising/central processing unit 60 (a CPU 60) that is in bidirectional communication with each module. While FIG. 3 schematically illustrates each module as being separate and distinct from other modules or the CPU, it should be understood that some or all modules may be implemented via a common integrated microcontroller or application-specific integrated circuit (ASIC). Further, in some embodiments the modules as illustrated may simply be representative of distinct functionality or software capabilities of the host processor 40. Regardless of the specific implementation, the following presents a summary of the various modules:

The stimulation generator 52 may be operative to generate a current-controlled electrical stimulus 22 that can be transmitted to an electrode 24 on the distal end of the stimulator 20. This electrical stimulus 22 may subsequently be administered to the intracorporeal tissue of the subject from the stimulator/electrode and returned to the unit via an associated ground patch that is adhered to the subject.

The electrical stimulus 22 generated by the stimulus generator 52 may, for example, be a periodic stimulus that includes a plurality of sequential discrete pulses (e.g., a step pulse) provided at a frequency of less than about 20 Hz, or between about 2 Hz and about 16 Hz. Each pulse may have a pulse width within the range of about 50 μs to about 400 μs. In other examples, each discrete pulse may have a pulse width within the range of about 50 μs to about 200 μs, or within the range of about 75 μs to about 125 μs. Additionally, in some embodiments, the current amplitude of each pulse may be independently controllable.

In some embodiments, the system may incorporate algorithms that automatically adjust the stimulation parameters, such as pulse width and frequency, based on the patient's real-time response and the stage of the decompression procedure. For instance, the system may start with a pulse width of 200 μs and a frequency of 4 Hz. If the elicited muscle response is weak or inconsistent, the system may automatically increase the pulse width to 300 μs to improve the sensitivity of the neuromonitoring. Conversely, if the muscle response is consistently strong, the system may reduce the pulse width to minimize the risk of nerve fatigue or injury. This adaptive approach may serve to optimize the stimulation parameters throughout the procedure, thus maintaining the reliability and specificity of the neuromonitoring.

If a nerve extends within a predetermined distance of the electrode 24, the electrical stimulus 22 may cause the nerve to depolarize, resulting in a mechanical twitch of a muscle that is innervated by the nerve (i.e., an artificially-induced mechanical muscle response). As noted above, each NMS 30 may be specially configured to monitor a local mechanical movement of an adjacent muscle group of the subject 14. In response to this sensed movement, each respective mechanical sensor 36 may generate a digital or analog mechanomyography (MMG) output signal 32 that corresponds to the sensed mechanical movement, force, and/or response of the adjacent muscle. The signal acquisition circuitry 54 of the processor 50 may be adapted to receive this MMG output signal 32 from the NMS 30, digitize it, condition and/or filter (if desired) it and make it available in memory for subsequent processing.

The display controller 56 may include any required memory or graphical processing units (GPUs) required to supply a display signal to the display 40. The communications circuitry 58 may include any required circuitry, wi-fi communication circuitry, BLUETOOTH communication circuitry, ethernet communication circuitry, modems, USB-C data transmission circuitry, wireless radio antennas, cellular communication chipsets, and/or any associated code to facilitate unidirectional or bidirectional digital communication between the processor 50 and external sources via either a wired or wireless communications protocol.

In some embodiments, the neural monitoring system 10 and/or display controller 56 may be integrated with intraoperative imaging modalities, such as fluoroscopy or ultrasound (i.e., "third party imaging" 42). In these configurations, the processor 50 may receive an imaging signal representative of an image or video, and the display controller 56 may then output the imaging from these external third-party imaging modalities 42 via the display 40. Integration of such third-party imaging modalities 42 may allow the surgeon to visualize the anatomical structures in real-time while simultaneously monitoring the nerve function. For example, the surgeon may use fluoroscopy to guide the placement of the stimulation probe and ensure that the electrode is in direct contact with the target nerve root. The fluoroscopic images, via the fluoro device/system may be received and displayed on the same screen as the neuromonitoring data, thus providing a comprehensive view of the surgical field. Similarly, ultrasound imaging may be used to assess the extent of decompression and identify any residual compression or nerve impingement. The ultrasound images can be correlated with the nerve function measurements, enabling the surgeon to make targeted adjustments to the decompression based on both anatomical and functional information.

The processor 50 (e.g., via the CPU 60) may include resident software, firmware, or embedded processing routines that are operative to analyze the output from the neuromuscular sensors 30 and identify muscle responses that were induced by an electrical stimulus 22 applied via the stimulator 20 (i.e., an artificially induced response). More specifically, these detection/identification techniques/algorithms may attempt to establish, with a high degree of confidence, that a detected muscle movement is the result of a nerve being artificially depolarized (i.e., via a stimulus 22 administered by the stimulator 20) and not simply a subject-intended muscle movement, an environmentally caused movement (e.g., bumping the operating table), or an artifact of another aspect of the procedure (e.g., sequential compression devices or cautery).

In varying embodiments, the detection techniques/algorithms may be performed in the analog/time domain, the digital/frequency domain, and/or may employ one or more wavelet analyses or multi-stage analysis techniques. Additional techniques such as response gating, stimulus frequency modulation, artificial intelligence/structured machine learning, and/or ensemble approaches may also be used to make this detection more robust and/or provide a greater degree of confidence in the detection. Examples of such detection techniques are described in greater detail in at least U.S. Pat. No. 8,343,065 (the '065 Patent"), issued on Jan. 1, 2013 (describing analog-domain detection techniques), U.S. Patent Publication No. 2015/0051506 (the '506 Publication), filed on Aug. 13, 2013 (describing digital/frequency-domain detection techniques), and U.S. Pat. No. 11,980,476 (the '476 Patent), issued on May 14, 2024 (describing wavelet detection techniques, response gaiting techniques, multi-stage detection techniques, variable frequency stimulation techniques, among others). Each of the '065 Patent, the '506 Publication, and the '476 Patent are incorporated by reference in their entirety and for all that they disclose.

Determination of Functional Parameters of the Nerve

To effectively monitor nerve function and guide the spinal decompression procedure, the present neural monitoring system 10 is configured to determine one or more functional parameters of the nerve through the performance and/or execution of one or more algorithms stored in memory associated with the processor 50. In a general these algorithms cause the administration of a controlled electrical stimulus 22 and then analyze the MMG output signals 32 generated as a result of the stimulus/stimulation to understand the functional status of the nerve. Examples of functional parameters that may be determined in this manner include one or more of: the minimum stimulation current that is required to elicit a detectable, threshold response in the muscle; the minimum stimulation current that is required to elicit a supramaximal response of the muscle; or the magnitude of the response of the muscle during a supramaximal contraction.

In some embodiments, the system 10 is configured to provide real-time feedback on nerve decompression progress by tracking changes in functional parameters throughout the surgery. This enables surgeons to make informed decisions about the extent of decompression needed and helps avoid situations of under- or over-decompression. In doing so, the system 10 may help identify potential residual compression or unrecognized nerve impingements before concluding the procedure. For instance, if parameters fail to improve as expected or plateau above a predefined target endpoint or range, the system may alert the surgeon to the possibility of residual compression. These insights may allow or encourage surgeons to further investigate the surgical field, using techniques like intraoperative imaging or direct visualization, to identify and/or address any remaining compression sources. By facilitating more complete and effective decompression through functional diagnostics, the system may reduce the risk of persistent postoperative symptoms and the need for revision surgery.

The determination of one or more of these functional parameters via the present system 10 provides objective criteria for assessing the decompression procedure intraoperatively. By comparing the parameter values to established normative ranges or patient-specific targets, the system can provide a clear indication of whether the decompression has achieved its intended goals or whether further intervention or investigation may be warranted.

The following describes examples of three functional parameters that may be used to quantitatively assess a nerve and provide evidence of neural compression:

Minimum Stimulation Current for Evoking Muscle Response (Stimulation Threshold)

The minimum stimulation current required to evoke a muscle response, also referred to as the "stimulation threshold," is the lowest electrical current intensity required to evoke a detectable or threshold-level muscle response in a muscle that is innervated by the nerve. Because the physical distance between the electrode 24 and the nerve impacts this threshold (i.e., a larger threshold current is required as the distance increases), it is preferable for this measure to be taken when the electrode 24 that is providing the stimulus 22 is in direct contact with the nerve. This parameter is a measure of nerve excitability and reflects the case with which the nerve can be stimulated to generate an action potential.

In the context of spinal decompression, monitoring the threshold current provides valuable information about the functional status of the compressed nerve. A high threshold current before decompression suggests that the nerve is less excitable, possibly due to the mechanical pressure exerted by the surrounding tissues. As the decompression progresses and the pressure on the nerve is relieved, the threshold current is expected to decrease, indicating improved nerve excitability.

The neural monitoring system 10 determines the threshold current by systematically varying the intensity of the electrical stimuli 22 delivered through the stimulator 20 (i.e., with the electrode 24 in direct or near-direct contact with the nerve). The processor 50 then analyzes the MMG output signals 32 to identify the minimum current intensity that consistently evokes a muscle response above a predefined amplitude threshold.

By tracking changes in the threshold current over the course of the decompression procedure, the system 10 can provide the surgeon with real-time feedback on the effectiveness of the decompression in restoring nerve excitability. A significant decrease in the threshold current compared to a pre-decompression baseline is generally considered a positive sign, indicating successful decompression and improved nerve function. Likewise, the threshold current falling within a predefined target range of current values can provide an indication that the nerve is no longer compressed. For clarity, the terms "minimum stimulation threshold" and "threshold current" are used interchangeably throughout this specification to refer to the lowest electrical current intensity required to evoke a detectable muscle response.

Minimum Stimulation Current for Supramaximal Muscle Response (Saturation Threshold)

The minimum stimulation current required to elicit a supramaximal response of the muscle, referred to as the "supramaximal threshold" or "saturation threshold," refers to the minimum electrical current intensity that is required to evoke the maximum achievable muscle response in a muscle that is innervated by the nerve. Like the threshold current described above, this parameter is also influenced by the distance between the electrode 24 and the nerve. Therefore, to remove variability, it is preferrable for the supramaximal threshold to be determined when the electrode 24 administering the stimulus 22 is in direct contact with the nerve.

The supramaximal threshold parameter provides information about the overall functional capacity of the nerve-muscle system and the number of motor units that can be recruited by the electrical stimulus. The supramaximal threshold generally represents the minimum electrical current level at which all available motor units in the muscle are recruited and depolarized, thus providing a measure of the overall functional capacity of the nerve-muscle system. During compression, the stimulation threshold for a supramaximal response may be elevated due to impaired nerve conduction or reduced responsiveness of the muscle.

In the context of spinal decompression, monitoring the supramaximal threshold (and changes in the threshold) can provide insights into the extent of acute or chronic nerve damage and the potential for functional recovery. A compressed nerve may exhibit a higher supramaximal threshold compared to a healthy nerve, suggesting that a larger proportion of motor units are not functioning properly, have decreased sensitivity, or require a greater stimulus current to be recruited. As the decompression progresses, this threshold is expected to decrease, indicating improved nerve function and muscle recruitment. The system 10 therefore may be configured to track changes in the supramaximal response threshold in an effort to provide additional guidance to the surgeon regarding the completeness of the decompression.

The neural monitoring system 10 determines the supramaximal stimulation threshold (the supramaximal threshold) by incrementally increasing the intensity of the electrical stimuli 22 beyond the threshold current until the amplitude of the MMG output signal 32 reaches a plateau. This plateau indicates that all available motor units are being recruited and that further increases in stimulation intensity do not result in a larger muscle response. Following this, the lowest current that elicits this plateau response is regarded as the supramaximal threshold. In some embodiments, the supramaximal threshold may be artificially defined as a current that induces a response that is a predefined percentage less than the magnitude of a full supramaximal response (e.g., 95% of the maximum achievable muscle response, or 90% of the maximum achievable muscle response, or even a percentage selected from the range of about 50% to about 100% of the maximum achievable muscle response).

In some embodiments, the system 10 may be configured to determine the supramaximal stimulation threshold by administering a plurality of pulses that each have a current intensity below the threshold. In doing so, the processor 50 may record a plurality of data points, where each data point includes a stimulus current value and an MMG output signal value. To then determine the threshold, the processor 50 may fit a curve through the recorded [stimulus current, MMG output signal] pairs and extrapolate this curve toward the threshold. (i.e., where the slope of the curve should decay toward zero as the current intensity is increased toward the threshold). In another embodiment, the system 10 may systematically increase the current level until multiple responses are achieved within a predefined error margin of each other (i.e., the plateau).

By comparing the supramaximal stimulation threshold before and after decompression, the system can assess the extent of functional recovery achieved by the decompression procedure. A significant decrease in the supramaximal stimulation threshold, accompanied by an increase in the magnitude of the muscle response, is generally considered a positive outcome, suggesting successful decompression and improved nerve function.

Magnitude of a Supramaximal Muscle Response

The magnitude of a supramaximal muscle response refers to the maximum strength or physical response of the muscle to a supramaximal electrical stimulus administered to the nerve innervating that muscle. Unlike the prior two parameters, supramaximal response magnitude is not affected by the distance between the electrode and the nerve as it is simply testing the maximum possible output from the nerve-muscle system and reflects the number and synchronization of motor units activated by the stimulus.

The magnitude of the supramaximal muscle response may be measured or quantified as one or more of: the maximum amplitude of the MMG output signal; the peak-to-peak amplitude of the MMG output signal; the root-mean-squared amplitude of the MMG output signal; or an area under the curve of the MMG output signal. This parameter provides valuable information about the strength and overall functional capacity of the nerve-muscle system. During compression, the magnitude of the supramaximal response may be diminished due to impaired nerve conduction and reduced motor unit recruitment. As the decompression procedure progresses and the nerve function improves, the magnitude of the muscle response to a given stimulus is expected to increase, thus reflecting the restored ability of the nerve to effectively activate the muscle. This increase in muscle response magnitude is often accompanied by a decrease in the stimulation thresholds (threshold current and supramaximal stimulation threshold), suggesting a comprehensive improvement in nerve function. The system 10 therefore may be configured to monitor changes in the supramaximal response magnitude to provide additional feedback to the surgeon regarding the effectiveness of the decompression.

The neural monitoring system 10 determines the magnitude of the muscle response by providing an electrical stimulus having a stimulation current that is at a known level at or above the supramaximal stimulation threshold. It then analyzes the MMG output signal to determine a peak response, an average response, or a power metric (e.g., the area under the curve of the MMG output signal 32) in response to that electrical stimulus. In certain scenarios, this parameter may be particularly valuable because the stimulation current can be selected at a level that is known to be greater than the supramaximal stimulation threshold, and thus direct contact between the electrode 24 and the nerve is not strictly required.

Method of Determining Functional Parameters of a Nerve

Measuring or quantifying the functional status of a nerve may involve determining one or more of the functional parameters described above (i.e., the minimum electrical current required to evoke a muscle response, the supramaximal stimulation threshold, and the magnitude of the supramaximal muscle response). If viewed together, these measurements may provide a comprehensive assessment of the nerve's overall functional status. As noted above, the processor 50 may use various techniques to determine one or more of the referenced nerve parameters. Once determined, Following a determination of one or more of the functional parameters of the nerve, the processor 50 may record the and may display the one or more determined parameters on the display 40 for the surgeon's reference. This display may take the form of displayed numerical values and/or graphs presenting the values and/or illustrating relative changes in the values. In one configuration, the stimulation threshold, supramaximal stimulation threshold, and magnitude of the supramaximal muscle response are displayed via the display along with one or more of a pre-procedure baseline value and/or a determined target endpoint value or range. Such a real-time display allows the surgeon to quickly interpret the results and make informed decisions about the course of the decompression procedure.

Example Nerve Parameter Determination Algorithm

In one particular algorithm, the processor 50 may employ a multi-stage approach to efficiently determine the functional parameters of the nerve while minimizing the total number of discrete stimuli required. This approach consists of two main stages:

Stage 1: A binary search algorithm efficiently locates the minimum stimulation threshold.

Stage 2: An adaptive search algorithm efficiently determines the supramaximal stimulation threshold by leveraging information from Stage 1.

This method reduces redundant stimuli, saves time, minimizes patient discomfort, and lowers the risk of nerve fatigue or injury from excessive stimulation. The efficiency of this approach allows for repeated assessments throughout the decompression process with minimal disruption to the overall surgical procedure.

By leveraging the data collected in the first stage to inform the next, the system reduces redundant stimuli and makes intelligent selections for stimulus currents in Stage 2. This approach not only saves time but also minimizes patient discomfort and the risk of nerve fatigue or injury from excessive stimulation. Furthermore, the efficiency and speed of the testing procedure enables repeated assessments throughout the decompression process while providing minimal disruption to the overall surgical procedure.

Stage 1: Determining the Minimum Stimulation Threshold

To begin the nerve function assessment, the surgeon may insert the stimulator probe 20 into or adjacent to the vertebral foramen and preferably places the electrode 24 in direct contact with the compressed nerve. Once the electrode is in position, the system 10 may be configured to initiate and perform a binary search algorithm (i.e., initiated by the surgeon) to efficiently determine the minimum stimulation threshold.

In one embodiment, the binary search algorithm may begin by defining a working range of stimulus intensities, typically 0-20 mA, which encompasses the expected minimum stimulation thresholds for both healthy and compressed nerves. The processor 50 then directs the stimulation generator 52 to generate an electrical stimulus 22 having a current at the midpoint of this range (e.g., 10 mA). This stimulus 22 is then transmitted through the electrode 24 to the nerve while the processor 50 simultaneously monitors for an evoked muscle response via the NMS 30 and signal acquisition circuitry 54.

If a response is detected, the processor 50 narrows the search range to the lower half of the previous range (e.g., 0-10 mA) and repeats the process, stimulating with a current at the new midpoint. Conversely, if no response is detected, the processor narrows the search range to the upper half (e.g., 10-20 mA). This process of halving the search range and stimulating at the midpoint current level continues until the minimum stimulation threshold is determined within a desired resolution, typically less than 1 mA.

By employing this binary search approach, the system can efficiently determine the minimum stimulation threshold with a small number of stimuli. For example, if the initial range is 0-20 mA, the minimum stimulation threshold can be determined within a resolution of 0.625 mA (i.e., 20 mA/$2^5$) using only five stimuli.

Stage 2a: Determining the Supramaximal Stimulation Threshold

After determining the minimum stimulation threshold in Stage 1, the system 10 proceeds to find the supramaximal stimulation threshold via a Stage 2 detection. To accomplish this efficiently, the processor 50 may leverage the stimulus-response data collected during the binary search process in Stage 1 to optimize the search for the supramaximal threshold.

In some embodiments, the processor 50 begins by analyzing the stimulus-response relationship observed during Stage 1. For example, the processor 50 may examine:

a) The rate of change in response magnitude as the stimulus intensity increased b) The final minimum stimulation threshold determined c) The shape of the stimulus-response curve at currents above the minimum threshold Based on this analysis, the processor 50 may then employ a predictive algorithm to estimate the likely range for the supramaximal threshold. For example, if no response was detected below 15 mA in Stage 1, the processor 50 might implement a binary search approach with a starting range of 15-50 mA (i.e., a range with a lower bound at or fractionally greater than the minimum stimulation threshold). The adaptive search algorithm may include analyzing the stimulus-response relationship observed during the binary search, including examining the rate of change in response magnitude, the determined minimum stimulation threshold, and the shape of the stimulus-response curve at currents above the minimum threshold. The algorithm may implement an adaptive binary search within the estimated range, testing the midpoint and adjusting the range based on whether the response shows signs of plateauing (e.g., an increase in response magnitude less than 10% compared to the previous point). The search may terminate when the increase in response magnitude between adjacent test points falls below a predefined threshold (e.g., 5%) or when the search range narrows to a predefined resolution (e.g., less than about 2 mA).

In another embodiment, the processor 50 may fit a preliminary stimulus-response curve to the data collected during Stage 1. The processor 50 may then extrapolate this curve to predict the approximate supramaximal stimulation threshold and use this prediction to identify an initial working range of currents to test.

Once the estimated range is determined, the processor 50 may then implement an adaptive binary search within this predicted range. As in stage 1, it may start by testing the midpoint of the range. If the response at this point shows signs of plateauing (i.e., the increase in response magnitude is less than, for example, 10% compared to the previous known point), the search focuses on the lower half of the range. If not, it searches the upper half. This process repeats, with dynamic adjustment of the threshold for plateauing as the search narrows.

As the stimulus intensity increases, the magnitude of the muscle response should also increase. However, at a certain intensity, the response magnitude will reach a plateau, indicating that the supramaximal stimulation threshold has been reached. The processor 50 identifies this plateau by comparing the magnitude of the muscle response at each stimulus current level to the response evoked by the previous current level.

In some embodiments, the search may terminate when one of two conditions is met:
- a) the increase in response magnitude between two adjacent test points falls below a predefined threshold (e.g., less than 5%); or
- b) the search range narrows to a predefined resolution (e.g., 0.5 mA)

The lowest current in the final search range is then recorded as the supramaximal stimulation threshold (i.e., the "saturation threshold").

By leveraging the stimulus-response data from Stage 1 and employing this adaptive search strategy, the system can efficiently determine the supramaximal stimulation threshold with a minimal number of additional stimuli. This approach not only saves time but also minimizes patient discomfort and the risk of nerve fatigue or injury from excessive stimulation, while ensuring accurate identification of the supramaximal threshold.

Stage 2b: Measuring the Magnitude of the Supramaximal Muscle Response

Once the supramaximal stimulation threshold has been determined, the processor 50 either through a subsequently generated/applied electrical stimulus 22, or via historical information, may measure and record the magnitude of the evoked muscle response to a stimulus having a current magnitude at (or above) the supramaximal stimulation threshold. This response magnitude, may be quantified as, for example, the maximum amplitude of the MMG output signal 32, the peak-to-peak magnitude of the MMG output signal 32; the root-mean-squared amplitude of the MMG output signal 32; or an area under the curve of the MMG output signal 32.

Nerve Function Index (NFI)

In some embodiments, the system 10 may be configured to calculate a composite nerve function index (NFI) that integrates multiple functional nerve parameters into a single metric or score. The NFI may serve as a comprehensive measure of nerve function and can be used to track the status of the nerve and/or the progress of the decompression across various points in the procedure. In some embodiments, the system 10 may also use the NFI to generate predictive models of surgical outcomes, helping surgeons to make more informed decisions about the optimal decompression endpoint.

In general, the primary components of the NFI may include the minimum stimulation current required to evoke a muscle response and the stimulation threshold for evoking a supramaximal muscle response. As noted above, these parameters are determined by the processor 50 through the controlled delivery of electrical stimuli 22 via the stimulator 20 and electrode 24, and through the simultaneous monitoring of muscle responses via the neuromuscular sensor 30/mechanical sensor 36.

In one example, to calculate the NFI, the processor 50 first determines the minimum stimulation current required to evoke a muscle response, the supramaximal stimulation threshold, and/or the supramaximal muscle response magnitude. In one embodiment, the NFI may be calculated as a weighted average of at least two of: the minimum electrical current required to evoke a muscle response, the supramaximal stimulation threshold, and the magnitude of the supramaximal muscle response. The processor 50 then combines these values into a composite index, for example, by computing a weighted average of the parameters (or normalized variants thereof), or by computing a respective probabilistic z-score for each parameter (i.e., against a population of similar parameters acquired from other individuals/procedures) and computing a weighted average of the z-scores. The weights assigned to each parameter may be based on their relative importance in assessing nerve function, as determined through empirical studies or expert consensus. In some embodiments, the system may allow for user input specifying the relative importance of different nerve function parameters. The processor 50 may then adjust the weights used in the weighted combination based on this user input, recalculate the nerve function index using the adjusted weights, and display the recalculated index on the display 40. In one embodiment, the weighted average may only consider the minimum stimulation current required to evoke a muscle response and the supramaximal stimulation threshold.

In another embodiment, instead of a weighted average, the NFI may be expressed as a ratio of the minimum stimulation threshold to the supramaximal stimulation threshold. For example, an NFI of 0.5 would indicate that the minimum stimulation current is half of the supramaximal stimulation threshold.

In addition to the minimum stimulation threshold, the supramaximal stimulation threshold, and/or the magnitude of the supramaximal muscle response, the processor 50 may also consider other factors when calculating the NFI. Such factors may include, for example and without limitation: latency of the muscle response; duration of the muscle response; the rate of change of nerve function parameters during a procedure or over a period of time; and/or the bilateral symmetry of nerve responses in the patient.

For clarity, "latency of the muscle" response generally refers to the time delay between the delivery of the electrical stimulus 22 and the onset of the muscle response. Such a metric may indicate the conduction velocity of the nerve, which can be affected by compression or other pathologies. The "duration of the muscle response" generally refers to the time of the muscle response, measured from onset to offset, which may reflect the synchronization and fatigability of the motor units, and can be impacted by nerve dysfunction. With respect to the rate of change of nerve function parameters, the processor 50 may track the changes in the minimum stimulation current, supramaximal stimulation threshold, and other parameters over time pre-surgery and/or during a decompression surgery. Rapid improvements in these parameters may indicate effective decompression, while plateaus or deteriorations in the rate of change may suggest the need for further intervention. Finally, in cases where bilateral nerve function measurements are available, the processor 50 may compare the NFI and/or any of the parameters discussed above between the patient's left and right sides. Significant asymmetries may indicate lateralized nerve dysfunction or the need for targeted/localized decompression.

Once the NFI is calculated, the processor 50 may display it to the surgeon via the display 40, along with the individual nerve function parameters and any relevant trends or comparisons. The NFI may be presented as a numerical value, a color-coded gauge, or a graphical representation, depending on the preferences of the user and the design of the user interface.

The NFI may serve as a valuable tool for assessing nerve function and guiding spinal decompression surgery. By providing a comprehensive, quantitative measure of nerve health, the NFI can help surgeons make informed decisions about the extent of decompression required, monitor the progress of the surgery, and evaluate the effectiveness of the intervention. The NFI may also be used to compare nerve function before and after the surgery, as well as to track long-term outcomes and guide postoperative care.

Target Ranges

During a surgical spinal decompression procedure, a primary objective is typically to alleviate compressive forces/pressure on a specific compressed nerve. In doing so, the procedure will ideally restore nerve function and/or reduce associated preoperative symptoms such as pain, numbness, and/or weakness. As the decompression procedure progresses and the compressive forces on the nerve are gradually relieved, the functional parameters of the nerve that are monitored by the neural monitoring system 10 (such as described above) are expected to exhibit improvement.

Figure 4:
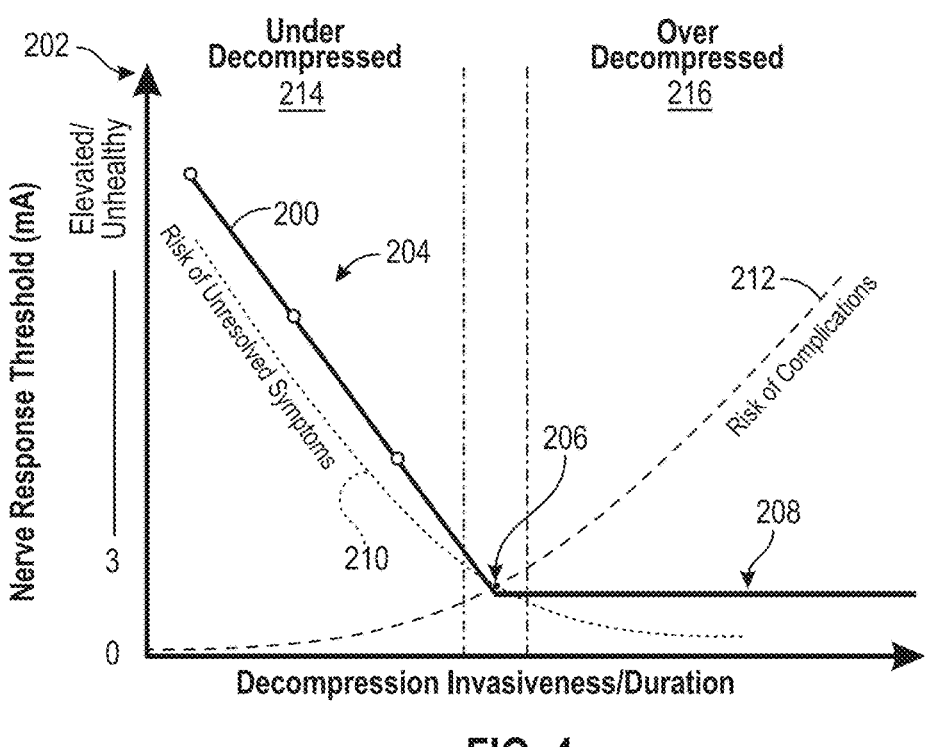
FIG. 4 schematically illustrates a graphical relationship of decompressive activity and stimulation threshold values.

While decompressive activity 200 and the nerve parameters 202 are initially related, such as generally shown at 204 in FIG. 4, there exists a critical point 206 during the decompression procedure at which the nerve becomes fully decompressed (i.e., the point at which all impinging tissue has been removed and the nerve is "free"). It is at this critical point 206 where further removal of surrounding bone or soft tissue (i.e., continued decompressive activity 200) will not yield additional functional improvement in the functional parameters 202, such as generally shown via the plateau at 208. Continuing the decompression beyond this critical point 206 may, in fact, result in "over-decompression," which can introduce unnecessary risks, including spinal instability, dural tears, or iatrogenic nerve injury.

As further illustrated in FIG. 4, absent other complicating factors or comorbidities, the critical point 206 also represents the point where both the risk of unresolved symptoms 210 and the risk of complications 212 are minimized. Said another way, the critical point 206 generally represents the point of optimality that separates under-decompression 214 (with elevated risks of unresolved symptoms) from over-decompression 216 (with elevated risks of complications).

During a surgical procedure, however, there is an inherent challenge in identifying the point 206 at which further decompressive activity 200 will yield minimal or no additional functional benefit. If the surgeon continues decompressing until the functional parameters completely flatten out, the patient may have already entered the realm of over-decompression 216 since confirming the plateau 208 necessitates additional surgical maneuvers and nerve function measurements, which may inadvertently cause harm to the nerve or surrounding structures.

Figure 5:
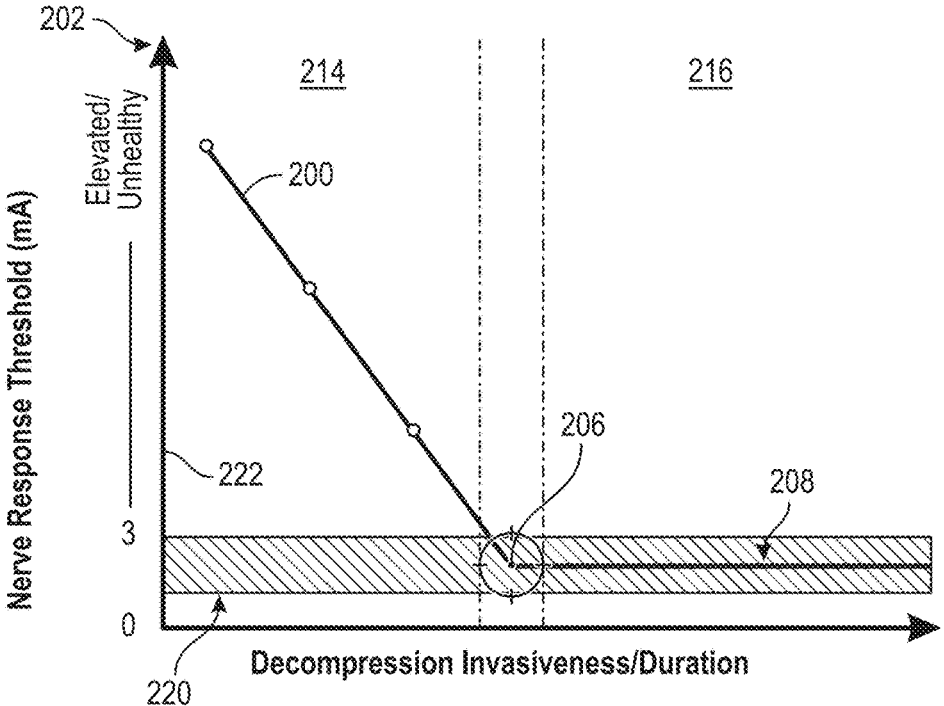
FIG. 5 schematically illustrates the graphical relationship of FIG. 4 with an overlaid target range.

To address this challenge, the neural monitoring system 10 employs the concept of a target range 220, such as shown in FIG. 5. The target range 220 generally represents a predefined, predictive and/or probabilistic range of values within which the critical point 206 and plateau 208 is likely to exist for a given parameter. Said another way, this range 220 is predictive of how the nerve should respond if fully decompressed and is largely dependent on patient physiology.

During a procedure, observing one or more nerve parameters entering its respective target range 220 may provide sufficient confirmation to a surgeon that a nerve is decompressed without the need to remove any additional bone or soft tissue to separately confirm the flattening out of the response. In many instances, particularly those where a decompression is warranted, the target range 220 represents a range of current values that is less than the initially determined minimum electrical current and also represents a range of values that are indicative of a fully decompressed nerve.

While each nerve parameter may have its own predetermined target range 220, FIGS. 4 and 5 specifically illustrate a graph of decompressive activity 200 and the stimulation threshold 222 parameter. The predefined target range 220 may be subject-specific and may be determined based on attributes including but not limited to age, body mass index (BMI), and pre-operative neurological function assessment. This individualized approach ensures tailored decompression for optimal patient outcomes. While the stimulation threshold target range 220 (i.e., representing a fully decompressed nerve) may vary from patient-to-patient based on factors such as the specific nerve being decompressed, the patient's age, and the presence of pre-existing nerve damage, in general, a target current range 220 of 2-3 mA or even 2-4 mA is considered to be a stimulation threshold that is indicative of a fully decompressed nerve in most healthy patients. As such, in one configuration, the system 10 may designate 2-4 mA as a baseline target current range 220 and may graphically identify this range 220 via an output on the display 40. In another embodiment, the baseline target current range may be established by testing a nerve exiting on the contralateral side of the spine and using the determined contralateral parameter to set an expected baseline target current range for the target nerve. In a similar manner, target ranges may also exist for supramaximal stimulation threshold and supramaximal muscle response to provide additional criteria indicative of a fully decompressed nerve.

While achieving nerve function parameters within the target range 220 does not guarantee a successful outcome (i.e., full resolution of symptoms) for every patient, it does signify that the decompression has reached a point where the risk-to-benefit ratio for any further intervention may be unfavorable. By using the target range 220 as a guide, surgeons can make informed decisions about when to conclude the decompression, reducing the likelihood of complications related to over-decompression.

Individualized Target Ranges

While generalized target ranges for nerve function parameters provide a valuable starting point for guiding spinal decompression surgery, they may not adequately address the unique characteristics and comorbidities of certain patients. More specifically, some conditions/comorbidities may cause the nerve to be generally less sensitive when decompressed than nerves in otherwise healthy patients. For example, older patients or those with chronic nerve compression may have a higher minimum stimulation threshold and a lower magnitude of the supramaximal muscle response at baseline, reflecting impaired nerve conduction and reduced muscle innervation. Conversely, younger patients or those with acute and/or mild nerve compression may be able to achieve comparatively lower thresholds due to a shorter duration of impingement and/or generally superior circulation and muscle tone.

Figure 6:
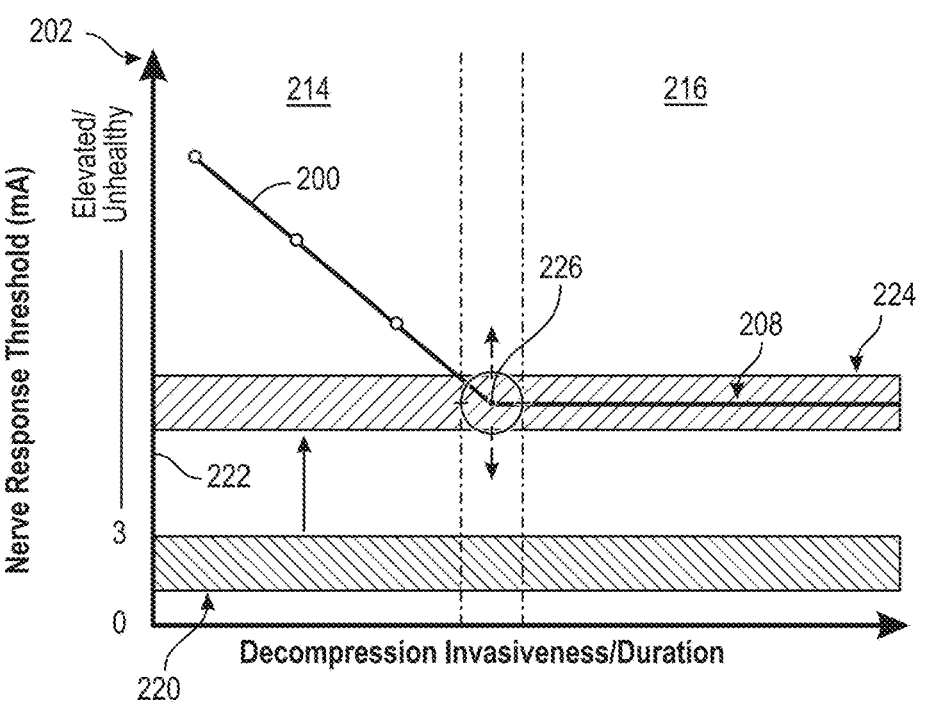
FIG. 6 schematically illustrates the graphical relationship of FIG. 5, with an overlaid patient-adjusted target range.

The concept of a patient-adjusted target range 224 is graphically illustrated in FIG. 6 in comparison to a more generalized initial baseline target current range 220. As shown, the patient-specific critical/inflection point 226 and patient-adjusted target range 224 may be elevated from the initial baseline target current range 220 due to patient-specific factors or comorbidities. As such, in one configuration, the system 10 may determine and display a patient-adjusted target current range 224 based on probabilistic models of a filtered patient population that more closely approximates condition and status of the specific patient.

By incorporating patient-specific factors/comorbidities into the determination of the target range, the neural monitoring system 10 may tailor the decompression endpoint to each patient's unique needs and neural physiology. Examples of patient-specific factors/cormorbidites that may be considered or may influence the target range include, without limitation, body mass index (BMI), diabetes, neuropathy, chronicity, duration of symptoms, medications, prior surgeries, or the presence of scar tissue. This individualized approach ensures that the extent of decompression is guided by the patient's specific neurological status and response to the procedure, rather than relying solely on generalized target ranges. By adjusting the target range based on patient factors, the system helps surgeons set realistic target goals for the procedure while optimizing the balance between achieving adequate decompression and minimizing the risk of complications.

Again, the target range attempts to predict (via statistical methods) how the patient's nerve will respond when fully decompressed. If adjusted to a specific patient, it recognizes that not all patients have the same neurophysiology, and a 2 mA stimulation threshold may not be achievable in certain patient populations. In this manner, the target range is a tool that the surgeon can use as a reference to guide surgical efforts toward a point of optimality (i.e., the threshold between under-decompressed 214 and over-decompressed 216) without doing too much or too little.

Intraoperative Adjustment of Target Ranges

In some embodiments, in addition to setting a patient-adjusted target current range 224 (generally determined pre-operatively) the neural monitoring system 10 may be capable of dynamically adjusting the patient-adjusted target range 224 based on real-time measurements and trends observed throughout the decompression procedure. This dynamic adjustment may account for factors such as the patient's individual response to decompression, the extent of nerve recovery, and any unexpected changes in nerve function.

To perform dynamic intraoperative target range adjustment, the processor 50 may continuously analyze the trend of any monitored functional parameters of the nerve throughout the procedure. The processor 50 may compare the rate of improvement in these parameters to expected trends based on the initial target ranges and the patient's profile. If parameters improve more rapidly than anticipated, the processor 50 may adjust the target ranges to reflect a more favorable surgical endpoint, potentially narrowing the range or shifting it towards more optimal values. Conversely, if parameters plateau or improve more slowly than expected, the processor 50 may widen the target range or shift it to accommodate the observed response. In cases of significant deviation from expected trends, the system 10 may prompt the surgeon to consider additional factors that may be influencing nerve recovery, such as residual compression or anatomical variations. In one particular embodiment, the system 10 may employ a Kalman filter to continuously update the optimal target range based on the observed rate of change in nerve function parameters and their deviation from the initial predicted ranges.

By dynamically adapting the target ranges according to the patient's real-time response, the system 10 may further ensure that the surgical endpoint remains optimized for each individual case. This dynamic adjustment capability may allow the system 10 to account for the variability in nerve function and response to decompression across different patients and surgical scenarios. The system's dynamic adjustment algorithm may utilize a combination of statistical methods and machine learning techniques to continuously refine the patient-adjusted target ranges. For instance, it may employ a Bayesian updating approach, where the initial target range (i.e., the prior distribution) is updated based on real-time measurements to produce a distribution that serves as the new, adjusted target range. This approach allows the system to balance pre-operative expectations with intraoperative realities, providing a more nuanced and personalized guidance throughout the procedure.

Method of Identifying Patient-Adjusted Target Range

In some embodiments, the target range 220 and/or patient-adjusted target range 224 may be selected via one or more statistical models of past patient data and outcomes (i.e., where "outcomes" generally refers to the ability for the procedure to resolve the symptoms that necessitated the procedure. Typically, successful outcomes involve the reduction or elimination of pain and/or the restoration of motor function, and can often be evidenced by a lack of subsequent therapeutic treatment for the same condition). In some embodiments, the generalized target range 220 may be representative of the outcomes/target range of entire population of past patient data and outcomes, however in other more preferred embodiments, the generalized target range 220 may be representative of a typical "best case scenario." In such an embodiment, the generalized target range 220 may be statistically determined by examining only a subset of the entire population that is regarded as "healthy" or lacking pre-existing conditions, comorbidities, or chronicity of the compression.

In contrast to the generalized target range 220, the patient-adjusted target range 224 may consider only a subset of the total patient population that has similar patient factors and/or comorbidities as the subject patient (though may be computed in generally similar manner)

Figure 7:
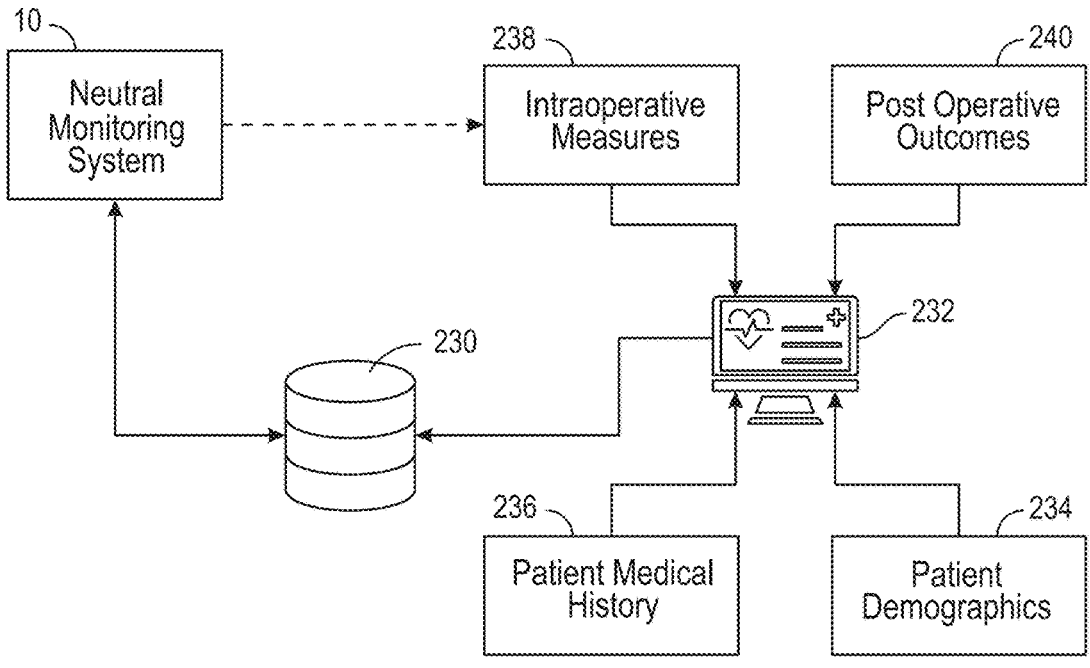
FIG. 7 schematically illustrates a functional diagram of the neural monitoring system in communication with a database.

As generally illustrated in FIG. 7, to determine the respective target range, the neural monitoring system 10 may be in communication with and configured to leverage a database 230 of previous surgical cases and their associated outcomes as the basis for setting the target range for a given procedure. Such a database 230 may include historical data obtained from, for example, an electronic medical record system 232 and/or input/generated from prior surgical cases. This data may include some or all of the following:

Patient Characteristics/Demographics 234: Age; gender; body mass index (BMI); race; geographic locale.

Patient Medical History 236: preexisting conditions/co-morbidities; duration and severity of symptoms; pre-operative neurological function; imaging findings.

Intraoperative Measurements/Data 238: Nerve function parameters (minimum stimulation threshold, supra-maximal stimulation threshold, and magnitude of the supramaximal muscle response) recorded at various stages of the decompression procedure; and surgical complications or technical challenges encountered during the procedure.

Post-operative outcome data 240: Clinical outcomes, such as pain relief, functional improvement, and patient satisfaction; and post-operative complications or the need for revision surgery.

When a new/subject patient undergoes spinal decompression surgery, the system 10 can query the database 230 to identify a subset of the total patient population that has similar patient characteristics/demographics 234 and/or patient medical history 236 as the subject patient. This process involves first obtaining patient characteristics/demographics from the subject patient and then filtering the total population of data within the database 230 to a subset that approximates the current patient's characteristic & medical history profile. Such a filtering process may consider any or all patient characteristics/demographics/history or it may rely on only a subset of the patient characteristics/demographics/history that have previously evidenced a statistical significance to surgical outcomes.

Once the relevant patient subset has been identified, the neural monitoring system 10 (or other local or remote processor) may analyze the relevant data from the filtered population to correlate intraoperative measures 238 with outcomes and/or complications 240. For example, in one embodiment, this analysis involves: constructing probabilistic distributions of surgical outcomes and complications as functions of terminal parameter measurements; identifying the range of values that maximize outcomes and/or minimize complications; setting this identified range as the patient-adjusted target range 224; and displaying the target range to the surgeon via the display 40. In some embodiments, the system 10 is configured to separately display outcome-specific and complication-specific distributions to the surgeon via the display 40, thus providing the surgeon with a more comprehensive view of the risk/reward balance.

Figure 8:
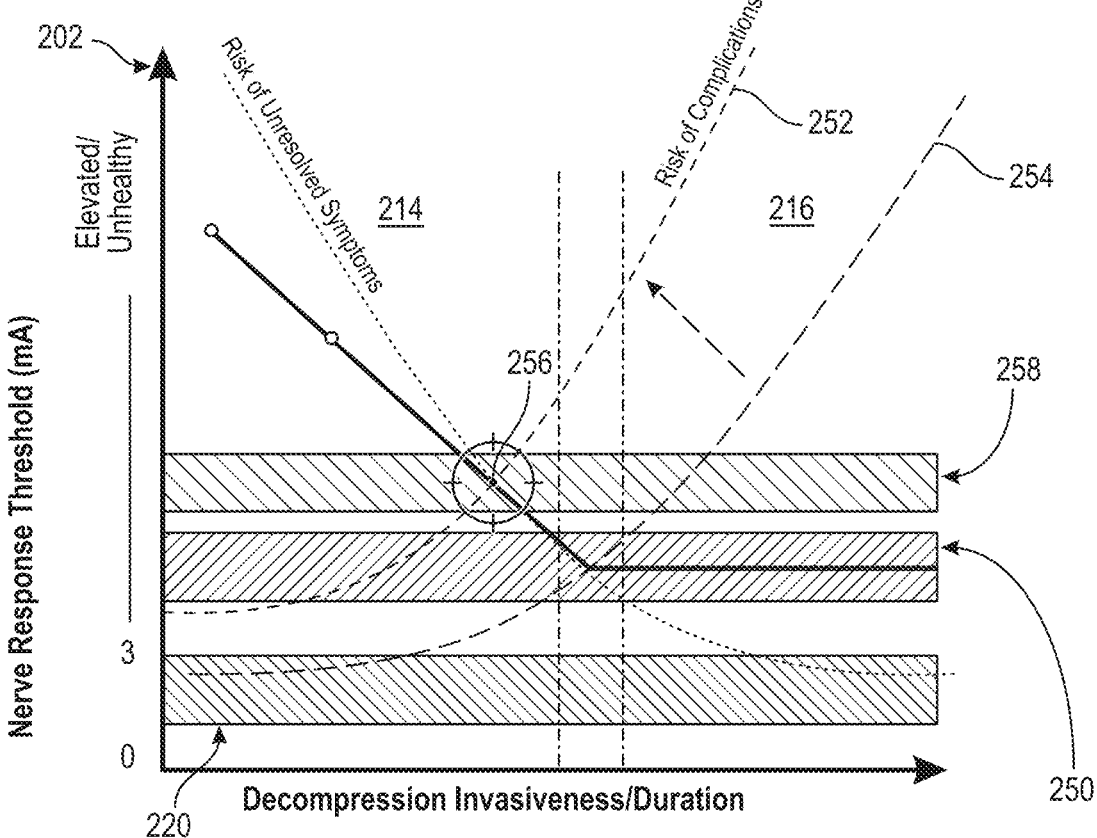
FIG. 8 schematically illustrates the graphical relationship of FIG. 6, with an overlaid estimate of procedural complications.

As a working example, the system 10 may begin by identifying a subset of patients within the database 230 that have a similar age, BMI, and pre-operative neurological assessments as the current patient. The system 10 may review the post-operative outcome data 240 for these patients and discover that the highest probability of a favorable surgical outcome (lowest risk of unresolved symptoms) was achieved at a minimum stimulation threshold between 3-5 mA and a supramaximal stimulation threshold between 10-14 mA. This initial step may focus entirely on outcomes and the ability for the procedure to alleviate the pre-operative symptoms that necessitated the procedure. As discussed above, this analysis is heavily tied to the subject's neural physiology and attempts to estimate the target range of parameter values where the nerve is no longer compressed. FIG. 8 generally illustrates this target range as the "Outcome-Adjusted Target Range" 250. Once determined, the system 10 may display this Outcome-Adjusted Target Range 250 to the surgeon via the display 40.

Separate from this range 250, the system 10 may also identify the statistical risk of complications for the subject patient as determined from the identified subset of similar patient within the database 230. As generally illustrated in FIG. 8, this patient-adjusted risk profile 252 may be expressed as a function of the monitored parameter 202, and in some embodiments, may vary from a baseline risk profile 254. In general, the baseline risk profile 254 may solely accounts for generalized procedural risks, whereas the patient-adjusted risk profile 252 may account for risks that may be more specific to the subject patient's specific characteristics 234 and/or history 236. In some embodiments, the system 10 may calculate the statistical risk of complications as a function of both the subject-specific attributes and the minimum electrical current of the electrical stimulus that is required to evoke a mechanical response of the muscle throughout the decompression procedure. In the illustrated embodiment, this patient-adjusted risk profile 252 may suggest that an optimal end point 256, or "Risk-Adjusted Target Range" 258 may result in a sub-optimal decompression (e.g., ending at a point that is technically under-decompressed), though avoids a significant increase in the risk of complications if a full decompression were attempted.

In some embodiments, the system 10 may calculate the statistical risk of complications 252, 254 using advanced statistical models, such as logistic regression or Cox proportional hazards models. These models may account for various factors including patient demographics, comorbidities, pre-operative condition, and intraoperative measurements. The system 10 may quantify the risk as a statistical chance of specific complications occurring. In a decompression, complications may include, for example, nerve injury, dural tears, hematoma, seroma, infection, or the need for revision surgery. This risk assessment may be static and/or predetermined prior to the procedure, or may be dynamically updated throughout the procedure based on the real-time nerve function measurements. As such, the system 10 may provide the surgeon with a continuously evolving risk profile to inform decision-making.

In other embodiments, instead of using a strict numeric probability, the system 10 may incorporate a tiered risk categorization scheme and classify the risk into categories such as "low", "moderate", and "high". This categorization can be visually represented on the display 40, for example, using a color-coded system (green for low risk, yellow for moderate risk, and red for high risk) to provide quick and intuitive feedback to the surgeon. Additionally, the system 10 may be configured to provide specific recommendations or precautions based on the current risk level, further assisting the surgeon in making informed decisions during the procedure.

Figure 9:
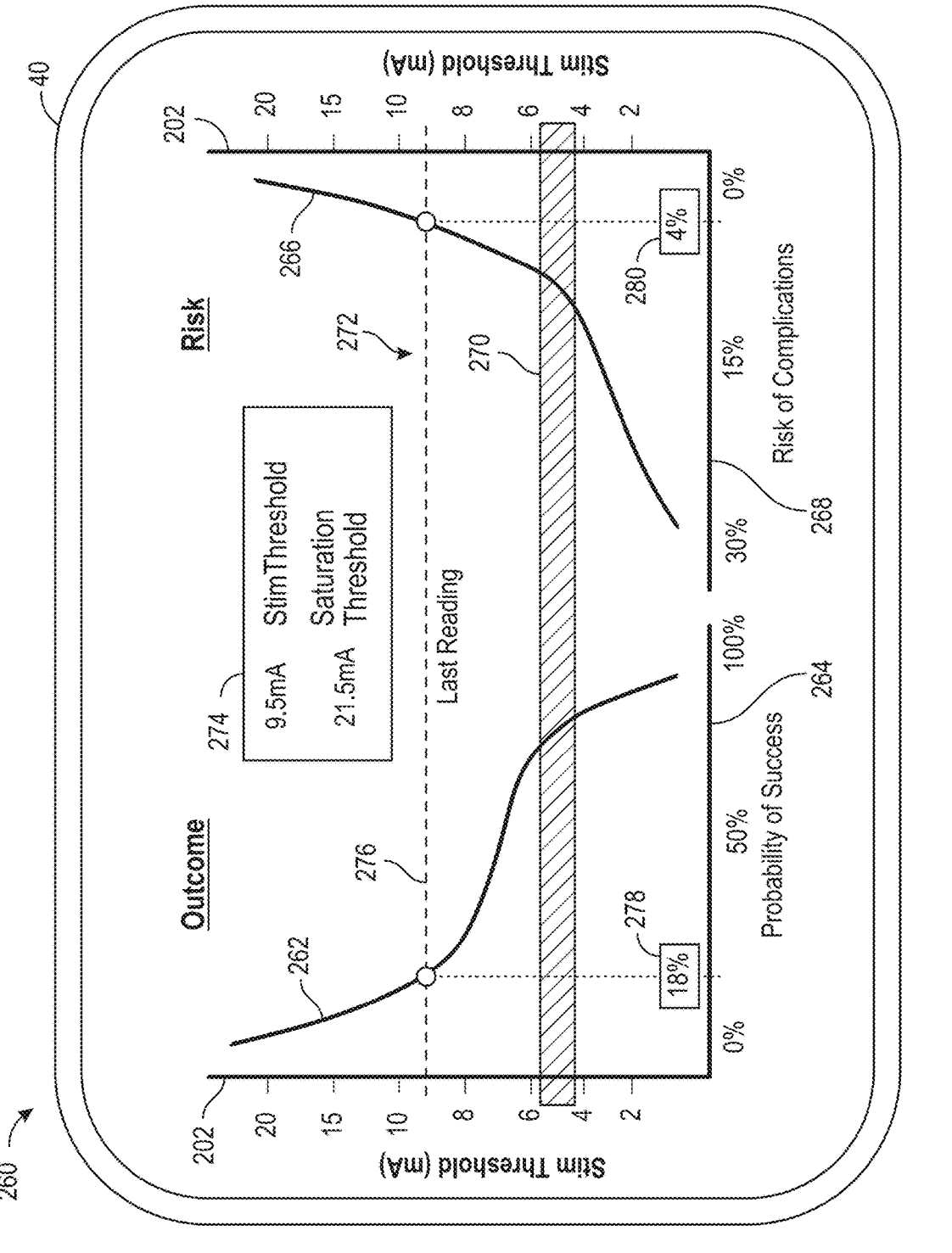
FIG. 9 schematically illustrates an embodiment of a display presenting a statistical profile of success and a statistical profile of the risk of complications as a function of stimulation threshold.

While FIG. 8 attempts to balance the risk of unresolved symptoms and the risk of complications with the patient's own physiology to arrive at a patient-adjusted target range, FIG. 9 illustrates a display 260 that separately presents both risk profiles to the surgeon. As shown, such a display 260 may include a first statistical profile 262 that illustrates the probabilistic likelihood of a successful outcome 264 as a function of the monitored functional parameter (e.g., stimulation threshold), and a second statistical profile 266 that illustrates the probabilistic risk of complications 268 as a function of the monitored functional parameter 202. These statistical profiles 262, 266 may be graphically represented, such as through a graph showing the individualized target range, a curve representing the statistical risk profile, an indicator showing the position of the measured nerve function parameter, a probability of successful outcome, and/or a risk of complications based on the measured parameter. In some embodiments, the system 10 may also provide an indication on the display 260 that estimates a possible or optimal target range 270 or surgical endpoint. Such a target range 270 may be surgeon-set, may be the outcome-adjusted target range 250, may be the risk-adjusted target range 258, and/or may be a range that optimizes a costing function that balances the probabilistic risk of unresolved symptoms with the risk of complications.

As further illustrated in FIG. 9, the display 260 may provide an indication 272 of the last measured reading for the parameter. Such a reading may include a graphical representation 274 and/or a textual representation 276. The display may then further correlate this reading with a real-time probability of success 278 and/or a real-time probabilistic risk of complications 280

Figure 10:
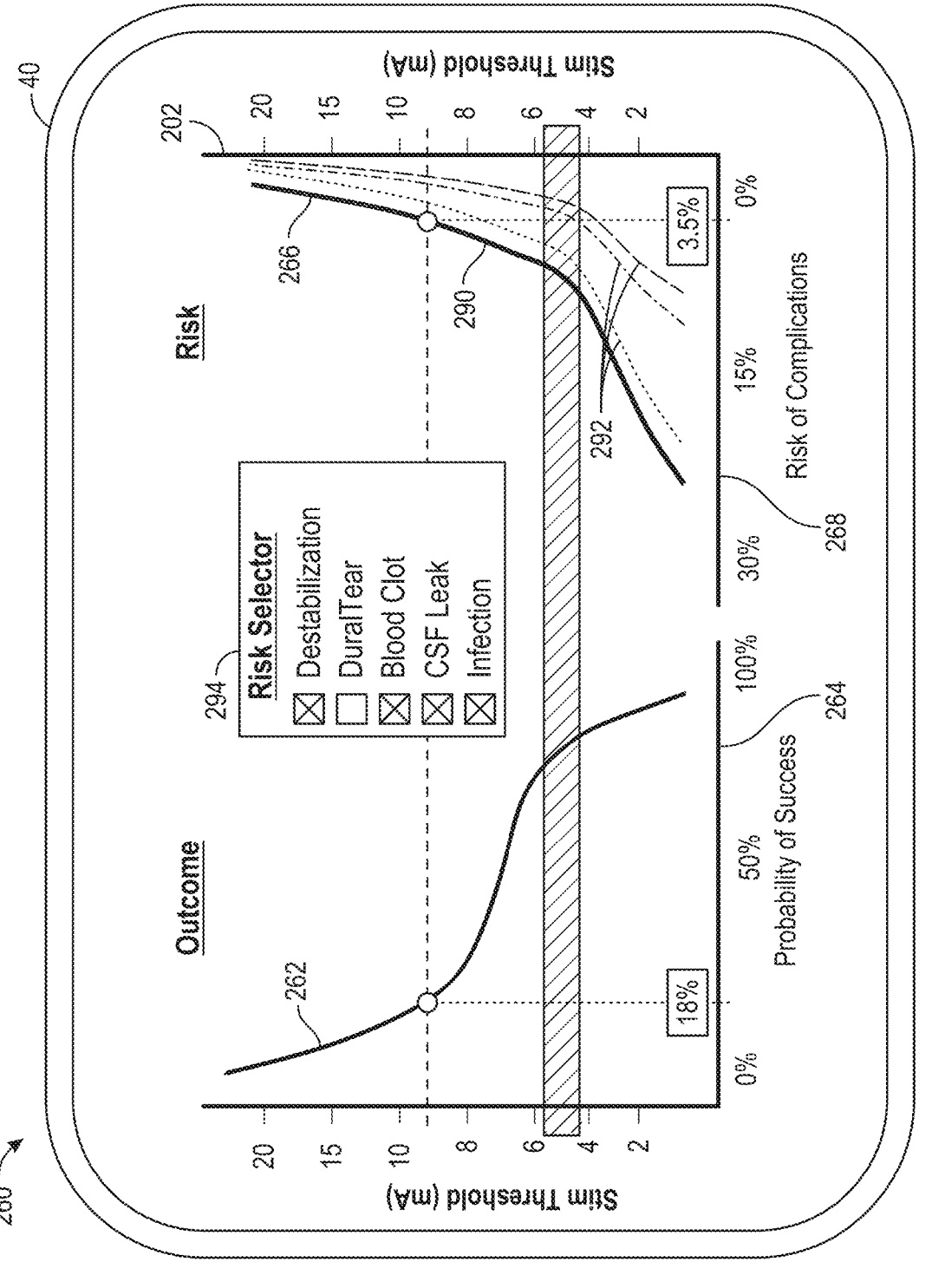
FIG. 10 schematically illustrates the display of FIG. 9, with a risk-selector tool operative to subdivide and filter a total risk of complications into several constituent statistical risk profiles.

As shown in FIG. 10, in some embodiments, statistical profile 266 illustrating the probabilistic risk of complications 268 may present an overall risk rate 290, may illustrate constituent risk rates 292, and/or may be customizable by the surgeon via a selection tool 294 to disregard certain risks that the surgeon may be less concerned with tracking. As such, in some embodiments, the statistical risk profile may include probabilities of specific surgical complications, such as destabilization of the spine, dural tears, blood clots, cerebrospinal fluid (CSF) leaks, or infections. In one example, if a surgeon is particularly adept at avoiding dural tears during a decompression, or if the procedure is such that a dural is less likely because of the location or nature of the decompression itself, then including the risk of dural tears in the overall risk rate 290 only serves to distort the true risks and a surgeon can therefore deselect this risk and remove it from the overall risk profile as shown.

As more surgical cases are added to the database 230, the neural monitoring system 10 can continuously refine its algorithms and improve the accuracy of its personalized target ranges and risk profiles. This refinement process may include receiving post-operative outcome data for each patient, updating the database with the patient's pre-operative characteristics, intraoperative nerve function measurements, and post-operative outcome data, and using machine learning algorithms to analyze patterns and associations between patient characteristics, nerve function parameters, and surgical outcomes to refine the process of generating individualized target ranges. By employing machine learning techniques, such as deep learning or reinforcement learning, the system can automatically identify complex patterns and relationships within the growing dataset, enabling more precise and adaptive target range adjustments and understandings of risk. In general, the machine learning techniques can identify patterns and associations between patient characteristics, neuroelectrical parameters, and surgical outcomes, thus allowing the system 10 to continuously refine the individualized target ranges for optimal decompression. For example, these techniques may identify that for patients with a specific combination of age, body mass index, and pre-operative symptoms, a slightly higher minimum stimulation threshold is associated with better outcomes and a lower risk of complications. The system can then dynamically adjust the target thresholds for the current patient based on these insights, ensuring that the decompression endpoint is tailored to their specific needs and circumstances.

In some embodiments, the system 10 may incorporate or be in direct communication with a dedicated machine learning module designed to continuously refine and improve the accuracy of the target ranges 270 and/or statistical profiles 262, 266. This module may employ one or more machine learning techniques, including, for example:

Supervised learning algorithms (e.g., random forests, gradient boosting machines, support vector machines) for predictive modeling of optimal target ranges based on patient characteristics and surgical parameters;

Unsupervised learning methods (e.g., k-means clustering) to identify subgroups of patients with similar response patterns to decompression; and/or Reinforcement learning approaches to optimize real-time decision-making and dynamic adjustment of target ranges during surgery based on immediate feedback and outcomes.

These algorithms in the machine learning module may be trained on historical data to identify complex patterns and relationships between patient characteristics, intraoperative measurements, and surgical outcomes that may not be apparent through traditional statistical analysis. For example, a support vector machine (SVM) algorithm might be used to determine the optimal criteria separating successful and unsuccessful surgical outcomes based on multiple input features, while a random forest algorithm could rank the importance of different patient characteristics in predicting optimal target ranges.

The machine learning module may be designed to continuously improve its performance by incorporating postoperative outcomes data into the learning process. This allows the system to optimize its target range recommendations based on actual patient results, rather than relying solely on intraoperative measurements. The module may automatically update, re-train, and fine-tune its models as new data is added to the database 230. This ongoing refinement process ensures that the system remains current with the latest clinical evidence and adapts to evolving surgical techniques and changing patient populations. By leveraging these advanced machine learning techniques, the system can provide increasingly accurate, personalized guidance for spinal decompression procedures over time.

Once the target range 270 and/or statistical profiles 262, 266 are determined from empirical data, they may then be stored in the processor 50 and displayed via the display 40 and in conjunction with actual readings taken during the procedure.

In some embodiments, a method for optimizing subject-specific spinal decompression surgery may be implemented by determining and utilizing individualized, patient-adjusted target ranges or statistical profiles that are a function of nerve function parameters. As discussed above, the neural monitoring system 10 comprises a stimulator 20 configured to deliver electrical stimuli 22 to a compressed nerve or nerve root within an intracorporeal treatment area 12 of a subject 14, a sensor 30 configured to detect muscle responses to the electrical stimuli 22, and a processor 50 in communication with both the stimulator 20 and the sensor 30.

The processor 50 is configured to receive subject-specific data, including age, gender, body mass index, and pre-operative neurological function, and to determine individualized thresholds for optimal spinal decompression based on this data. The processor 50 is further configured to monitor nerve function by controlling the stimulator 20 via the stimulation generator 52 and analyzing signals from the sensor 30 via the signal acquisition circuitry 54. The monitored nerve function is then compared to the individualized thresholds or target ranges, and the processor 50 provides real-time guidance to the user via the display 40, which is controlled by the display controller 56, to achieve optimal spinal decompression based on this comparison.

The method for determining and utilizing individualized target ranges begins with the processor 50 receiving an indication of the subject patient's demographic and medical history data. Following this, the processor 50 (and/or a processor in digital communications with the processor 50) may access a broader database 230 of subject data comprising nerve function measurements obtained during previous spinal decompression procedures and their associated subject outcomes. The processor 50 (or coupled device) then identifies a subset of subjects in the database 230 with similar characteristics to the current subject 14 undergoing spinal decompression. Based on this subset, the processor 50 may determine a target level of nerve function associated with successful outcomes and/or one or more statistical profiles of success, residual symptoms, and/or risk of complications and may display these target ranges or profiles to the user/surgeon. Slightly restated, the method may include: accessing a database containing historical patient data, including pre-operative characteristics, intraoperative nerve function measurements, and post-operative outcomes; receiving patient data of the current patient; identifying a subset of historical patients with similar pre-operative characteristics; generating an individualized target range for at least one nerve function parameter based on the subset; measuring, during the procedure, at least one actual nerve function parameter of the current patient; and displaying a graphical representation of the measured parameter relative to the individualized target range. In some embodiments, the processor 50 may utilize an estimated risk of complications to adjust the target range to a level that may present suboptimal surgical outcomes though may provide a lower total cost of care by minimizing secondary risk.

Throughout the spinal decompression procedure, the processor 50 measures the subject's nerve function at one or more time points using the stimulator 20 and neuromuscular sensor (NMS) 30. The measurements may involve determining a minimum electrical current required to evoke a muscle response, a current required to evoke a supramaximal muscle response, and the magnitude of the supramaximal muscle response. These measurements may then (optionally) be used to calculate a nerve function index to provide a more simplified, yet comprehensive assessment of nerve health and function.

The measured nerve function or calculated nerve function index is then compared by the processor 50 to the patient-adjusted target level, range, and/or statistical profile that was determined from the subset of similar subjects and may output this comparison to the display 40. The processor 50 may further provide real-time guidance to the surgeon, via the display 40, indicating whether the target level of nerve function has been achieved. This guidance may include displaying the minimum electrical current relative to the individualized target current range, generating audible or visual alerts when the measured nerve function reaches the target level, or providing other relevant feedback.

To further refine the individualized target ranges or statistical profiles, the processor 50 may employ a machine learning module. This module analyzes intraoperative neuromonitoring data and subject outcomes from the database of previous spinal decompression surgeries to identify patterns and associations. Based on this analysis, the module refines the individualized thresholds for optimal spinal decompression, allowing for continuous improvement of the target ranges as more data becomes available.

In some embodiments, the processor 50 may also dynamically adjust the individualized thresholds based on the monitored nerve function and intraoperative neuromonitoring data obtained during the current subject's spinal decompression surgery. This allows for real-time adaptation of the target ranges based on the subject's individual response to the decompression procedure.

The processor 50 may also track changes in the nerve function index throughout the spinal decompression surgery to assess the effectiveness of the decompression. By comparing the changes in the current subject's nerve function index to the range of baseline nerve function indices associated with successful outcomes in the subset of similar subjects, the processor 50 can provide additional guidance to the surgeon regarding the progress and adequacy of the decompression. The processor 50 may also determine a probabilistic measure of success for the spinal decompression procedure based on the nerve function index, using a statistical model derived from historical patient outcomes. This probabilistic measure of success may be displayed to the surgeon via the display 40.

While the system has been primarily described in the context of spinal decompression surgery, its principles and methods can be adapted for use in other surgical procedures involving nerve monitoring. For example, the system could be applied to peripheral nerve decompression surgeries, such as carpal tunnel release or cubital tunnel release. In these cases, the target ranges and risk assessments would be adjusted to reflect the specific characteristics of the nerves involved. The system could also be adapted for use in tumor resection surgeries near critical nerve structures, where real-time feedback on nerve function could help surgeons maximize tumor removal while minimizing nerve damage.

While various embodiments of the present technology have been described with varying levels of complexity, it should be understood that the present disclosure relates to a method of determining and displaying one or more nerve function parameters, including, but not limited to: stimulation threshold, saturation threshold, and/or magnitude of a supramaximal muscle response. In some embodiments, these determined parameters may be compared to target ranges, or plotted on statistical profiles to provide guidance to a surgeon during a decompression procedure. Such target ranges and/or statistical profiles may be derived/determined from a database of prior patient/procedure data that includes intraoperative parameter measurements, patient demographics, patient medical history, and/or prior surgical outcomes and complications. While stimulation threshold is often used as an example parameter for the purpose of illustration, the present disclosure should not be strictly limited to the use of stimulation threshold as a functional parameter unless specified in the claims. The present disclosure further teaches examples of methods for obtaining multiple functional parameters in a streamlined and efficient manner, and for combining multiple parameters into a single Nerve Function Index. Aspects of the disclosed technology aim to provide surgeons with evidence-based insights into the decompression procedure that have not previously been available. Finally, while spinal decompression procedures are the primary focus of the present concepts in this disclosure, it should be appreciated that these concepts and measures can be useful in other medical/neurological disciplines where a functional understanding of nerve health and performance is warranted.

"A", "an", "the", "at least one", and "one or more" are used interchangeably to indicate that at least one of the items is present. A plurality of such items may be present unless the context clearly indicates otherwise. All numerical values of parameters (e.g., of quantities or conditions) in this specification, unless otherwise indicated expressly or clearly in view of the context, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, a disclosure of a range is to be understood as specifically disclosing all values and further divided ranges within the range.

The terms "comprising", "including", and "having" are inclusive and therefore specify the presence of stated features, steps, operations, elements, or components, but do not preclude the presence or addition of one or more other features, steps, operations, elements, or components. Orders of steps, processes, and operations may be altered when possible, and additional or alternative steps may be employed. As used in this specification, the term "or" includes any one and all combinations of the associated listed items. The term "any of" is understood to include any possible combination of referenced items, including "any one of" the referenced items. The term "any of" is understood to include any possible combination of referenced claims of the appended claims, including "any one of" the referenced claims.

The following examples provide additional and/or alternative embodiments of the presently disclosed technology. Each example system and/or method should be read in light of the details provided above and is included strictly to supplement the present disclosure in a non-limiting manner.

Example 1. A system for assessing nerve decompression during a spinal surgical procedure comprises: a stimulator (20) configured to deliver electrical stimuli to a nerve; a sensor (30) configured to detect muscle responses evoked by the electrical stimuli; a display (40); and a processor (50) configured to: control the stimulator to deliver the electrical stimuli to the nerve; determine a nerve function parameter based on the muscle responses detected by the sensor; compare the determined nerve function parameter to a predefined target range; and control the display to provide an indication of the comparison between the determined nerve function parameter and the predefined target range.

Example 2. The system described in example 1, wherein the nerve function parameter is a minimum electrical current of the electrical stimuli required to evoke a detectable muscle response.

Example 3. The system described in example 1 or 2, wherein the predefined target range is indicative of a fully decompressed nerve.

Example 4. The system described in any one of the preceding examples, wherein the predefined target range is a range of electrical currents that includes at least the range of 2 mA to 3 mA.

Example 5. The system described in any one of the preceding examples, wherein the predefined target range is subject-specific and is determined based on one or more subject-specific attributes including age, body mass index (BMI), or pre-operative neurological function assessment.

Example 6. The system described in example 5, wherein the processor is further configured to: access a database of historical data comprising nerve function measurements obtained during previous surgical procedures, subject-specific attributes, and associated surgical outcomes; identify a subset of subjects in the database with attributes similar to a subject undergoing the spinal surgical procedure; and define the predefined target range based on nerve function parameters associated with successful outcomes in the identified subset of subjects.

Example 7. The system described in any one of the preceding examples, wherein the sensor (30) comprises a mechanical sensor with an accelerometer configured to detect a mechanical muscle response evoked by the electrical stimuli.

Example 8. The system described in any one of the preceding examples, wherein the processor is further configured to: determine a statistical risk of complications based on the nerve function parameter and subject-specific attributes; and control the display to provide an indication of the statistical risk of complications.

Example 9. The system described in any one of the preceding examples, wherein the nerve function parameter is a nerve function index comprising a weighted average of at least two of: a minimum electrical current required to evoke a detectable muscle response; a minimum electrical current required to evoke a supramaximal muscle response; and a magnitude of the supramaximal muscle response.

Example 10. A method of operating a system for assessing nerve decompression during a spinal surgical procedure comprises: delivering, by a stimulator (20), electrical stimuli to a nerve; detecting, by a sensor (30), muscle responses evoked by the electrical stimuli; determining, by a processor (50), a nerve function parameter based on the detected muscle responses; comparing, by the processor, the determined nerve function parameter to a predefined target range; and controlling, by the processor, a display (40) to provide an indication of the comparison between the determined nerve function parameter and the predefined target range.

Example 11. The method described in example 10, wherein the nerve function parameter is a minimum electrical current of the electrical stimuli required to evoke a detectable muscle response.

Example 12. The method described in example 10 or 11, wherein the predefined target range is indicative of a fully decompressed nerve.

Example 13. The method described in any one of examples 10 to 12, wherein the predefined target range is a range of electrical currents that includes at least the range of 2 mA to 3 mA.

Example 14. The method described in any one of examples 10 to 13, wherein the predefined target range is subject-specific and is determined based on one or more subject-specific attributes including age, body mass index (BMI), or pre-operative neurological function assessment.

Example 15. The method described in example 14, further comprising: accessing a database of historical data comprising nerve function measurements obtained during previous surgical procedures, subject-specific attributes, and associated surgical outcomes; identifying a subset of subjects in the database with attributes similar to a subject undergoing the spinal surgical procedure; and defining the predefined target range based on nerve function parameters associated with successful outcomes in the identified subset of subjects.

Example 21. A system for determining nerve parameters comprises: a stimulator (20) configured to deliver electrical stimuli to a nerve; a sensor (30) configured to detect muscle responses evoked by the electrical stimuli and generate mechanomyography (MMG) output signals; a display device (40); and a processor (50) configured to: generate a series of electrical stimuli with controlled current intensities; receive the MMG output signals from the sensor; determine a minimum stimulation threshold using a binary search algorithm based on the MMG output signals; determine a supramaximal stimulation threshold using an adaptive search algorithm based at least in part on MMG output signals obtained during the binary search algorithm; and control the display device to display at least one of the minimum stimulation threshold or the supramaximal stimulation threshold.

Example 22. The system described in example 21, wherein the binary search algorithm comprises: defining an initial current range for the electrical stimuli; selecting a midpoint of the initial current range; applying a first electrical stimulus with a current magnitude at the midpoint of the current range; detecting whether a muscle response is evoked via the first electrical stimulus; and iteratively performing the following steps until the minimum stimulation threshold is determined within a predefined resolution: defining a new current range based on the detection of a muscle response to the prior electrical stimulus; applying an electrical stimulus with a current magnitude at the midpoint of the new current range; and detecting whether a muscle response is evoked via the electrical stimulus.

Example 23. The system described in example 22, wherein the initial current range is from 0 mA to 20 mA.

Example 24. The system described in example 22 or 23, wherein the predefined resolution is less than or equal to 2 mA.

Example 25. The system described in any one of examples 21-24, wherein the adaptive search algorithm comprises: analyzing a stimulus-response relationship observed during the binary search algorithm; estimating an initial range for the supramaximal stimulation threshold based on the analysis; implementing an adaptive binary search within the estimated range; and identifying the supramaximal stimulation threshold based on a detected plateau in muscle response magnitude.

Example 26. The system described in example 25, wherein analyzing the stimulus-response relationship includes examining at least one of: a rate of change in response magnitude as stimulus intensity increased; the determined minimum stimulation threshold; or a shape of a stimulus-response curve at currents above the minimum stimulation threshold.

Example 27. The system described in example 25 or 26, wherein the adaptive binary search comprises: generating an electrical stimulus having a current magnitude at a midpoint of the estimated range to determine a response of the muscle; testing on a lower half of the range if the response of the muscle to the electrical stimulus at the midpoint shows signs of plateauing; and testing on an upper half of the range if the response of the muscle to the electrical stimulus at the midpoint does not show signs of plateauing.

Example 28. The system described in example 27, wherein signs of plateauing are detected when an increase in response magnitude is less than 10% compared to a previous known point.

Example 29. The system described in any one of examples 5 to 8, wherein the adaptive binary search terminates when: an increase in response magnitude between two adjacent test points falls below a predefined threshold; or the search range narrows to a second predefined resolution.

Example 30. The system described in example 29, wherein the predefined threshold is 5% and the second predefined resolution is less than or equal to 2 mA.

Example 31. The system described in any one of examples 21-30, wherein the processor is further configured to determine a magnitude of a supramaximal muscle response by analyzing a muscle response evoked by a stimulus at or above the supramaximal stimulation threshold.

Example 32. The system described in any one of examples 21-31, wherein the processor is further configured to: access a database of historical nerve function measurements and associated patient outcomes; identify a subset of patients in the database with characteristics similar to a current patient; and determine a target range for at least one of the minimum stimulation threshold or the supramaximal stimulation threshold based on nerve function measurements associated with successful outcomes in the subset of patients.

Example 33. The system described in example 32, wherein the processor is further configured to control the display device to display a visualization of the at least one of the minimum stimulation threshold or the supramaximal stimulation threshold relative to the determined target range.

Example 34. The system described in any one of examples 21-34, wherein the processor is further configured to calculate a nerve function index by computing a weighted average of at least two of: the minimum stimulation threshold, the supramaximal stimulation threshold, and a magnitude of a supramaximal muscle response.

Example 35. A method of operating a system for determining nerve parameters, the method comprising: generating, by a processor (50), a series of electrical stimuli with controlled current intensities; transmitting the series of electrical stimuli to a stimulator (20) in electrical communication with a nerve; receiving, by the processor, mechanomyography (MMG) output signals from a sensor (30) in mechanical communication with a muscle innervated by the nerve; determining, by the processor, a minimum stimulation threshold using a binary search algorithm based on the MMG output signals; determining, by the processor, a supramaximal stimulation threshold using an adaptive search algorithm based at least in part on the MMG output signals obtained during the binary search algorithm; and controlling, by the processor, a display device (40) to display at least one of the minimum stimulation threshold or the supramaximal stimulation threshold.

Example 41. A system for assessing nerve health during a spinal surgical procedure, the system comprising: a database (230) containing historical patient data; a stimulator (20) configured to deliver electrical stimuli to a nerve; a sensor (30) configured to detect muscle responses evoked by the electrical stimuli; a display device (40); and a processor (50) configured to: access the historical patient data; identify a subset of historical patients similar to a current patient; generate an individualized target range for at least one nerve function parameter based on the subset of historical patients; control the stimulator to deliver the electrical stimuli; analyze signals from the sensor to determine at least one actual nerve function parameter; control the display device to display a graphical representation of the actual nerve function parameter relative to the individualized target range.

Example 42. The system described in example 41, wherein the historical patient data includes pre-operative characteristics, intraoperative nerve function measurements, and post-operative outcomes.

Example 43. The system described in example 41 or 42, wherein the processor is further configured to: generate a statistical risk profile correlating nerve function measurements with probabilities of surgical complications based on the subset of historical patients; and compare the actual nerve function parameter to the statistical risk profile.

Example 44. The system described in example 43, wherein the processor is further configured to control the display device to display a graphical representation of the actual nerve function parameter relative to the statistical risk profile.

Example 45. The system described in example 44, wherein the graphical representation includes: a graph showing the individualized target range for the at least one nerve function parameter; a curve representing the statistical risk profile; an indicator showing the position of the actual nerve function parameter relative to the graph and the curve; a probability of successful outcome based on the actual nerve function parameter; and a risk of complications based on the actual nerve function parameter.

Example 46. The system described in any one of examples 41-45, wherein the at least one nerve function parameter includes at least one of: minimum stimulation threshold, supramaximal stimulation threshold, and magnitude of supramaximal muscle response.

Example 47. The system described in any one of examples 41-46, wherein the processor is configured to identify the subset of historical patients by applying a machine learning algorithm to the historical patient data to cluster patients based on similarity of pre-operative characteristics.

Example 48. The system described in any one of examples 41-47, wherein the processor is further configured to calculate a nerve function index based on multiple nerve function measurements, and wherein the individualized target range is generated for the nerve function index.

Example 49. The system described in any one of examples 43 to 48, wherein the statistical risk profile includes probabilities of specific surgical complications, including at least one of: a destabilization of the spine, a dural tear, a blood clot, a cerebrospinal fluid (CSF) leak, or an infection.

Example 50. The system described in any one of examples 41-49, wherein the sensor (30) is a mechanomyography (MMG) sensor configured to detect mechanical muscle responses.

Example 51. The system described in any one of examples 41-50, wherein the processor is further configured to: receive post-operative outcome data for the current patient; update the database with the current patient's pre-operative characteristics, intraoperative nerve function measurements, and post-operative outcome data; and refine the process of generating individualized target ranges based on the updated database.

Example 52. The system described in example 51, wherein the processor is configured to refine the process of generating individualized target ranges by using a machine learning algorithm to analyze patterns and associations between patient characteristics, nerve function parameters, and surgical outcomes.

Example 53. The system described in any one of examples 41-52, wherein the processor is further configured to generate an alert when the actual nerve function parameter enters the individualized target range.

Example 54. A method of operating a system for assessing nerve health during a spinal surgical procedure, the method comprising: accessing, by a processor (50), a database (230) containing historical patient data; receiving, by the processor, patient data of a current patient; identifying, by the processor, a subset of historical patients with characteristics similar to the current patient; generating, by the processor, an individualized target range for at least one nerve function parameter based on the subset of historical patients; controlling, by the processor, a stimulator (20) to deliver electrical stimuli to a nerve of the current patient; analyzing, by the processor, signals from a sensor (30) to determine at least one actual nerve function parameter; and controlling, by the processor, a display device (40) to display a graphical representation of the actual nerve function parameter relative to the individualized target range.

Example 55. The method described in example 54, further comprising: generating, by the processor, a statistical risk profile correlating nerve function measurements with probabilities of surgical complications based on the subset of historical patients; comparing, by the processor, the actual nerve function parameter to the statistical risk profile; and controlling, by the processor, the display device to display a graphical representation of the actual nerve function parameter relative to the statistical risk profile.

Example 61. A system for assessing nerve health during a spinal surgical procedure, the system comprising: a stimulator (20) configured to deliver electrical stimuli to a nerve; a mechanical sensor (30) configured to detect muscle responses evoked by the electrical stimuli; a memory; a display device (40); and a processor (50) configured to: control the stimulator to deliver a series of electrical stimuli, analyze signals from the sensor to determine a plurality of nerve function parameters, calculate a nerve function index based on a weighted combination of the determined nerve function parameters, store the nerve function index in the memory, and control the display device to display the nerve function index.

Example 62. The system described in example 61, wherein the plurality of nerve function parameters include at least two of: a minimum stimulation threshold; a supramaximal stimulation threshold; and a magnitude of a supramaximal muscle response.

Example 63. The system described in example 61 or 62, wherein the processor is further configured to: identify a nerve function index target range; and control the display device to display the nerve function index relative to the nerve function index target range.

Example 64. The system described in any one of examples 61-63, wherein the processor is configured to calculate the nerve function index by normalizing each of the determined nerve function parameters before combining them.

Example 65. The system described in any one of examples 61-64, wherein the processor is configured to dynamically adjust the weights used in the weighted combination based on at least one of: the specific nerve being assessed; or the stage of the spinal surgical procedure.

Example 66. The system described in any one of examples 61-65, wherein the processor is further configured to: calculate multiple nerve function indices, each at a different respective time during the spinal surgical procedure; and control the display device to display a trend of the nerve function index over time.

Example 67. The system described in any one of examples 61-66, wherein the processor is further configured to: determine a probabilistic measure of success for the spinal surgical procedure based on the nerve function index, wherein the probabilistic measure is calculated using a statistical model derived from historical patient outcomes; and control the display device to display the probabilistic measure of success.

Example 68. The system described in any one of examples 61-67, wherein the processor is further configured to: access a database of historical patient data including pre-operative characteristics, intraoperative nerve function indices, and post-operative outcomes; identify a subset of historical patients with characteristics similar to a current patient; determine a target range for the nerve function index based on outcomes of the identified subset of historical patients; and control the display device to display the target range with the calculated nerve function index.

Example 69. The system described in any one of examples 61-68, wherein the processor is configured to calculate the nerve function index by: multiplying each parameter by an assigned weight; and summing the weighted parameters to produce the nerve function index.

Example 70. The system described in any one of examples 61-69, wherein the processor is further configured to: determine a quantified degree of nerve decompression based on the nerve function index; and control the display device to display an indication of the quantified degree of nerve decompression.

Example 71. The system described in any one of examples 61-70, wherein the processor is further configured to: receive a user input specifying a relative importance of different nerve function parameters; adjust the weights used in the weighted combination based on the user input; recalculate the nerve function index using the adjusted weights; and control the display device to display the recalculated nerve function index.

Example 72. The system described in any one of examples 61-71, wherein the mechanical sensor (30) is a mechanomyography (MMG) sensor configured to detect mechanical muscle responses.

Example 73. A method of operating a system for assessing nerve health during a spinal surgical procedure, the method comprising: controlling, by a processor (50), a stimulator (20) to deliver a series of electrical stimuli to a nerve; analyzing, by the processor, signals from a mechanical sensor (30) to determine a plurality of nerve function parameters based on muscle responses evoked by the electrical stimuli; calculating, by the processor, a nerve function index based on a weighted combination of the determined nerve function parameters; storing, by the processor, the nerve function index in a memory; and controlling, by the processor, a display device (40) to display the nerve function index.

Example 74. The method described in example 73, further comprising: identifying, by the processor, a nerve function index target range; controlling, by the processor, the display device to display the nerve function index relative to the nerve function index target range.

Example 75. The method described in example 73 or 74, further comprising: accessing, by the processor, a database of historical patient data including pre-operative characteristics, intraoperative nerve function indices, and post-operative outcomes; identifying, by the processor, a subset of historical patients with characteristics similar to a current patient; determining, by the processor, a target range for the nerve function index based on outcomes of the identified subset of historical patients; and controlling, by the processor, the display device to display the target range with the calculated nerve function index.

Example 81. A system for assessing nerve health during a spinal surgical procedure, the system comprising: a database (230) containing historical patient data; a stimulator (20) configured to deliver electrical stimuli to a nerve; a sensor (30) configured to detect muscle responses evoked by the electrical stimuli; a display device (40); and a processor (50) configured to: access the historical patient data; apply a machine learning algorithm to the historical patient data to identify patterns between pre-operative characteristics, intraoperative nerve function measurements, and post-operative outcomes; generate, based on the identified patterns, a predictive model for estimating surgical outcomes; control the stimulator to deliver the electrical stimuli; analyze signals from the sensor to determine at least one actual nerve function parameter; input the at least one actual nerve function parameter into the predictive model to estimate a surgical outcome for a current patient; control the display device to display the estimated surgical outcome.

Example 82. The system described in example 81, wherein the machine learning algorithm comprises at least one of: a supervised learning algorithm, an unsupervised learning algorithm, or a reinforcement learning algorithm.

Example 83. The system described in example 81 or 82, wherein the processor is further configured to: cluster historical patients in the database based on similarity of pre-operative characteristics using the machine learning algorithm; identify a cluster of historical patients similar to the current patient; and generate an individualized target range for the at least one actual nerve function parameter based on the identified cluster of historical patients.

Example 84. The system described in any one of examples 81-83, wherein the processor is further configured to: continuously update the predictive model during the spinal surgical procedure based on real-time measurements of the at least one actual nerve function parameter.

Example 85. The system described in any one of examples 81-84, wherein the processor is further configured to: apply a machine learning algorithm to analyze intraoperative trends in the at least one actual nerve function parameter; and predict, based on the analyzed trends, a likelihood of the at least one actual nerve function parameter reaching a target range.

Example 86. The system described in any one of examples 81-85, wherein the processor is further configured to: calculate a nerve function index based on a weighted combination of multiple nerve function parameters; apply a machine learning algorithm to dynamically adjust the weights used in the weighted combination based on the specific characteristics of the current patient and the stage of the spinal surgical procedure.

Example 87. The system described in any one of examples 81-86, wherein the processor is further configured to: apply a machine learning algorithm to generate a statistical risk profile correlating nerve function measurements with probabilities of surgical complications; compare the at least one actual nerve function parameter to the statistical risk profile; and control the display device to display a predicted risk of complications based on the comparison.

Example 88. The system described in any one of examples 81-87, wherein the processor is further configured to: receive post-operative outcome data for the current patient; update the database with the current patient's pre-operative characteristics, intraoperative nerve function measurements, and post-operative outcome data; and retrain the machine learning algorithm using the updated database to improve the accuracy of the predictive model.

Example 89. The system described in any one of examples 81-88, wherein the machine learning algorithm comprises a neural network trained to recognize patterns in nerve function parameters that are indicative of successful surgical outcomes.

Example 90. The system described in any one of examples 81-89, wherein the processor is further configured to: apply a machine learning algorithm to identify optimal stimulation parameters for assessing nerve function based on patient-specific characteristics and real-time feedback from the sensor.

Example 91. The system described in any one of examples 81-90, wherein the processor is further configured to: apply a machine learning algorithm to analyze the muscle responses detected by the sensor and automatically distinguish between responses evoked by the electrical stimuli and other muscle movements.

Example 92. A method of operating a system for assessing nerve health during a spinal surgical procedure, the method comprising: accessing, by a processor (50), a database (230) containing historical patient data; applying, by the processor, a machine learning algorithm to the historical patient data to identify patterns between pre-operative characteristics, intraoperative nerve function measurements, and post-operative outcomes; generating, by the processor based on the identified patterns, a predictive model for estimating surgical outcomes; controlling, by the processor, a stimulator (20) to deliver electrical stimuli to a nerve of a current patient; analyzing, by the processor, signals from a sensor (30) to determine at least one actual nerve function parameter; inputting, by the processor, the at least one actual nerve function parameter into the predictive model to estimate a surgical outcome for the current patient; and controlling, by the processor, a display device (40) to display the estimated surgical outcome.

Example 93. The method described in example 92, further comprising: clustering, by the processor, historical patients in the database based on similarity of pre-operative characteristics using the machine learning algorithm; identifying, by the processor, a cluster of historical patients similar to the current patient; and generating, by the processor, an individualized target range for the at least one actual nerve function parameter based on the identified cluster of historical patients.

Example 94. The method described in example 92 or 93, further comprising: continuously updating, by the processor, the predictive model during the spinal surgical procedure based on real-time measurements of the at least one actual nerve function parameter.

Example 95. The method described in any one of examples 92 to 94, further comprising: receiving, by the processor, post-operative outcome data for the current patient; updating, by the processor, the database with the current patient's pre-operative characteristics, intraoperative nerve function measurements, and post-operative outcome data; and retraining, by the processor, the machine learning algorithm using the updated database to improve the accuracy of the predictive model.

Example 101. A system for improving nerve health assessment in spinal surgical procedures, the system comprising: a database (230) containing historical patient data; a processor (50) configured to: access the database to retrieve historical patient data, including pre-operative characteristics, intraoperative nerve function measurements, and post-operative outcomes; analyze the historical patient data to identify correlations between the pre-operative characteristics, intraoperative nerve function measurements, and post-operative outcomes; generate a predictive model based on the identified correlations; receive new patient data including pre-operative characteristics and intraoperative nerve function measurements for a completed surgical procedure; apply the predictive model to the new patient data to generate a predicted post-operative outcome; receive actual post-operative outcome data for the completed surgical procedure; compare the predicted post-operative outcome with the actual post-operative outcome; update the predictive model based on the comparison; and store the updated predictive model in the database for use in future surgical procedures.

Example 102. The system described in example 101, wherein the processor is further configured to: categorize the historical patient data into subgroups based on similarities in pre-operative characteristics; generate separate predictive models for each subgroup; and select an appropriate predictive model for the new patient data based on the pre-operative characteristics of the new patient.

Example 103. The system described in example 101 or 102, wherein the intraoperative nerve function measurements comprise at least one of: minimum stimulation threshold, supramaximal stimulation threshold, and magnitude of supramaximal muscle response.

Example 104. The system described in any one of examples 101-103, wherein the processor is configured to analyze the historical patient data using machine learning techniques to identify non-linear relationships between the pre-operative characteristics, intraoperative nerve function measurements, and post-operative outcomes.

Example 105. The system described in any one of examples 101-104, wherein the processor is further configured to: identify outliers in the historical patient data where the actual post-operative outcomes significantly deviate from the predicted post-operative outcomes; and analyze the outliers to identify additional factors that may influence surgical outcomes.

Example 106. The system described in any one of examples 101-105, wherein the processor is further configured to: generate confidence intervals for the predicted post-operative outcomes based on the variability in the historical patient data.

Example 107. The system described in any one of examples 101-106, wherein the post-operative outcomes include at least one of: pain reduction, functional improvement, or need for revision surgery.

Example 108. The system described in any one of examples 101-107, wherein the processor is further configured to: analyze long-term follow-up data to assess the durability of surgical outcomes; and incorporate the long-term follow-up data into the predictive model.

Example 109. The system described in any one of examples 101-108, wherein the processor is further configured to: identify trends in the accuracy of the predictive model over time; and generate alerts if the accuracy of the predictive model falls below a predetermined threshold.

Example 110. The system described in any one of examples 101-109, wherein the processor is further configured to: analyze the effectiveness of different surgical techniques based on the historical patient data and post-operative outcomes; and incorporate information about surgical techniques into the predictive model.

Example 111. The system described in any one of examples 101-110, further comprising: a display device (40); wherein the processor is further configured to control the display device to present a user interface for inputting new patient data and viewing predicted post-operative outcomes.

Example 112. A method of operating a system for improving nerve health assessment in spinal surgical procedures, the method comprising: accessing, by a processor (50), a database (230) to retrieve historical patient data, including pre-operative characteristics, intraoperative nerve function measurements, and post-operative outcomes; analyzing, by the processor, the historical patient data to identify correlations between the pre-operative characteristics, intraoperative nerve function measurements, and post-operative outcomes; generating, by the processor, a predictive model based on the identified correlations; receiving, by the processor, new patient data including pre-operative characteristics and intraoperative nerve function measurements for a completed surgical procedure; applying, by the processor, the predictive model to the new patient data to generate a predicted post-operative outcome; receiving, by the processor, actual post-operative outcome data for the completed surgical procedure; comparing, by the processor, the predicted post-operative outcome with the actual post-operative outcome; updating, by the processor, the predictive model based on the comparison; and storing, by the processor, the updated predictive model in the database for use in future surgical procedures.

Example 113. The method described in example 112, further comprising: categorizing, by the processor, the historical patient data into subgroups based on similarities in pre-operative characteristics; generating, by the processor, separate predictive models for each subgroup; and selecting, by the processor, an appropriate predictive model for the new patient data based on the pre-operative characteristics of the new patient.

Example 114. The method described in example 112 or 113, further comprising: analyzing, by the processor, long-term follow-up data to assess the durability of surgical outcomes; and incorporating, by the processor, the long-term follow-up data into the predictive model.

Example 115. The method described in any one of examples 112 to 114, further comprising: analyzing, by the processor, the effectiveness of different surgical techniques based on the historical patient data and post-operative outcomes; and incorporating, by the processor, information about surgical techniques into the predictive model.

The invention claimed is:

1. A method for intraoperative guidance during a surgical procedure involving a nerve, the method performed by a system comprising a processor, the method comprising:

receiving, by the processor, real-time image data from an intraoperative imaging modality, the real-time image data depicting anatomical structures within an intracorporeal treatment area including the nerve;

determining, by the processor based on signals received from a sensor configured to detect muscle responses evoked by electrical stimuli applied near the nerve, a value of at least one nerve function parameter indicative of nerve health;

determining, by the processor, a statistical risk of complications based on the value of the at least one nerve function parameter;

controlling, by the processor, a display device to concurrently present a visual output comprising both a visual representation derived from the real-time image data and a visual indication of the determined at least one nerve function parameter, wherein the visual indication of the determined at least one nerve function parameter includes at least one of:

a numerical or graphical representation of the value of the nerve function parameter;

a numerical or graphical representation of a difference between the value of the nerve function parameter and a target range for the value of the nerve function parameter; or a color-coded representation of the value of the nerve function parameter; and controlling, by the processor, the display device to present a visual representation of the statistical risk of complications alongside the visual indication of the determined at least one nerve function parameter.

2. The method of claim 1, wherein the intraoperative imaging modality comprises at least one of: fluoroscopy or ultrasound.

3. The method of claim 1, wherein concurrently presenting the visual output includes displaying the visual indication of the determined at least one nerve function parameter overlaid onto the visual representation derived from the real-time image data.

4. The method of claim 1, further comprising:

correlating, by the processor, the determined at least one nerve function parameter with one or more specific anatomical structures visible in the real-time image data; and wherein controlling the display device comprises presenting the visual indication of the determined at least one nerve function parameter in relation to the one or more specific anatomical structures within the visual output.

5. The method of claim 4, wherein the visual indication of the determined at least one nerve function parameter is displayed spatially correlated with a representation of the nerve or the one or more specific anatomical structures within the visual representation derived from the real-time image data.

6. The method of claim 1, wherein the at least one nerve function parameter includes at least one of: a minimum stimulation threshold, a supramaximal stimulation threshold, or a magnitude of a maximal muscle response.

7. The method of claim 1, wherein the sensor comprises a mechanomyography (MMG) sensor configured to detect a mechanical muscle response evoked by the electrical stimuli; and wherein determining the at least one nerve function parameter comprises:

generating, by the processor, one or more electrical stimuli;

transmitting the one or more electrical stimuli to an electrode positioned near the nerve;

receiving, by the processor, the signals from the sensor indicative of the muscle responses evoked by the one or more electrical stimuli; and analyzing, by the processor, the received signals to determine the at least one nerve function parameter.

8. The method of claim 1, further comprising:

receiving, by the processor, tracking data indicative of a location of a stimulator used to apply the electrical stimuli; and displaying, by the processor via the display device, the location of the stimulator within the visual representation derived from the real-time image data.

9. The method of claim 8, further comprising determining nerve function parameters at a plurality of different stimulator locations and generating the concurrently presented visual output to display a map of nerve function correlated with the anatomical structures.

10. The method of claim 1, wherein the surgical procedure is a spinal decompression procedure, the method further comprising using the concurrently presented visual output to assess an extent of nerve decompression based on both the visual representation of the anatomical structures and the visual indication of the determined at least one nerve function parameter.

11. A system for providing integrated intraoperative guidance during a surgical procedure involving a nerve, the system comprising:

an imaging interface configured to receive real-time image data from an intraoperative imaging modality, the real-time image data depicting anatomical structures within an intracorporeal treatment area including the nerve;

a sensor configured to detect muscle responses evoked by electrical stimuli applied near the nerve and generate sensor signals indicative thereof;

a display device; and a processor communicatively coupled to the imaging interface, the sensor, and the display device, the processor configured to:

receive the real-time image data via the imaging interface;

determine, based on the sensor signals, a value of at least one nerve function parameter indicative of nerve health;

determine a statistical risk of complications based on the value of the at least one nerve function parameter;

control the display device to concurrently present a visual output comprising both a visual representation derived from the real-time image data and a visual indication of the determined at least one nerve function parameter, wherein the visual indication of the determined at least one nerve function parameter includes at least one of:

a numerical or graphical representation of the value of the nerve function parameter;

a numerical or graphical representation of a difference between the value of the nerve function parameter and a target range for the value of the nerve function parameter; or a color-coded representation of the value of the nerve function parameter; and control the display device to present a visual representation of the statistical risk of complications alongside the visual indication of the determined at least one nerve function parameter.

12. The system of claim 11, wherein the intraoperative imaging modality comprises at least one of: fluoroscopy or ultrasound.

13. The system of claim 11, wherein the processor is configured to control the display device to present the visual indication of the determined at least one nerve function parameter overlaid onto the visual representation derived from the real-time image data.

14. The system of claim 11, wherein the processor is further configured to:

correlate the determined at least one nerve function parameter with one or more specific anatomical structures visible in the real-time image data; and control the display device to present the visual indication of the determined at least one nerve function parameter in relation to the one or more specific anatomical structures within the visual output.

15. The system of claim 14, wherein the processor is configured to control the display device to present the visual indication of the determined at least one nerve function parameter spatially correlated with a representation of the nerve or the one or more specific anatomical structures within the visual representation derived from the real-time image data.

16. The system of claim 11, wherein the at least one nerve function parameter includes at least one of: a minimum stimulation threshold, a supramaximal stimulation threshold, or a magnitude of a maximal muscle response.

17. The system of claim 11, wherein the sensor comprises a mechanomyography (MMG) sensor, the MMG sensor including an accelerometer configured to detect a mechanical muscle response evoked by the electrical stimuli; and wherein the processor is configured to determine the at least one nerve function parameter by:

generating one or more electrical stimuli;

transmitting the one or more electrical stimuli to an electrode positioned near the nerve;

receiving the signals from the sensor indicative of the muscle responses evoked by the one or more electrical stimuli; and analyzing the received signals to determine the at least one nerve function parameter.

18. The system of claim 11, wherein the processor is further configured to:

access a database containing historical patient data including pre-operative characteristics, intraoperative nerve function parameters, and post-operative outcomes;

identify a subset of historical patients with characteristics similar to a subject undergoing the surgical procedure;

generate an individualized target range for the at least one nerve function parameter based on the subset of historical patients; and control the display device to present the determined at least one nerve function parameter relative to the individualized target range within the visual output.

19. A method for intraoperative guidance during a surgical procedure involving a nerve, the method performed by a system comprising a processor, the method comprising:

receiving, by the processor, real-time image data from an intraoperative imaging modality, the real-time image data depicting anatomical structures within an intracorporeal treatment area including the nerve;

determining, by the processor based on signals received from a sensor configured to detect muscle responses evoked by electrical stimuli applied near the nerve, a value of at least one nerve function parameter indicative of nerve health; and controlling, by the processor, a display device to concurrently present a visual output comprising both a visual representation derived from the real-time image data and a visual indication of the determined at least one nerve function parameter, wherein the visual indication of the determined at least one nerve function parameter includes at least one of:

a numerical or graphical representation of the value of the nerve function parameter;

a numerical or graphical representation of a difference between the value of the nerve function parameter and a target range for the value of the nerve function parameter; or a color-coded representation of the value of the nerve function parameter; and wherein the at least one nerve function parameter comprises a nerve function index calculated as a weighted average of at least two of: a minimum stimulation threshold, a supramaximal stimulation threshold, and a magnitude of a supramaximal muscle response.

* * * * *